US012754300B2

(12) United States Patent
Zhang et al.

(10) Patent No.: US 12,754,300 B2
(45) Date of Patent: Oct. 6, 2026

(54) TRANSDUCER MODULE ARCHITECTURE FOR ENHANCING SENSITIVITY OF AN ULTRASOUND SYSTEM

(71) Applicant: FUJIFILM SonoSite, Inc., Bothell, WA (US)

(72) Inventors: Jimin Zhang, Bellevue, WA (US); Wei Li, Bothell, WA (US); Andrew Lundberg, Woodinville, WA (US)

(73) Assignee: FUJIFILM SonoSite, Inc., Bothell, WA (US)

( * ) Notice: Subject to any disclaimer, the term of this patent is extended or adjusted under 35 U.S.C. 154(b) by 389 days.

(21) Appl. No.: 18/400,058

(22) Filed: Dec. 29, 2023

(65) Prior Publication Data

US 2025/0216526 A1 Jul. 3, 2025

(51) Int. Cl.
*G01S 7/52* (2006.01)
*A61B 8/00* (2006.01)

(52) U.S. Cl.
CPC ........ *G01S 7/52023* (2013.01); *A61B 8/4483* (2013.01); *G01S 7/52019* (2013.01); *G01S 7/52085* (2013.01)

(58) Field of Classification Search
CPC ............. G01S 7/52023; G01S 7/52019; G01S 7/52085; A61B 8/4483; A61B 8/56; A61B 8/5207; A61B 8/54; A61B 8/4494
See application file for complete search history.

(56) References Cited

U.S. PATENT DOCUMENTS 5,178,150 A 1/1993 Silverstein et al.
6,432,055 B1 8/2002 Carp et al.
(Continued)

FOREIGN PATENT DOCUMENTS

CN 112050981 A * 12/2020 ......... G01N 29/2412
CN 117225674 A * 12/2023
(Continued)

OTHER PUBLICATIONS

Translation of JP-2004097588 (Year: 2004).*
(Continued)

*Primary Examiner* — Daniel Pihulic
(74) *Attorney, Agent, or Firm* — Colby Nipper PLLC

(57) ABSTRACT

Systems and methods for implementing a transducer module architecture that enhances sensitivity of an ultrasound system are described. To enhance sensitivity while using a transducer element for transmission and reception, a transducer module's architecture provides operation-specific impedance matching. Operation-specific impedance matching means that different impedances are provided for mitigating mismatch loss during transmission and reception. The impedance provided for reception can be associated with separate signal path with a smaller amount of attenuation compared to the impedance provided for transmission. In this way, the architecture enhances sensitivity of the ultrasound system by reducing an amount of attenuation experienced during reception compared to other ultrasound systems that utilize a same impedance for impedance matching during transmission and reception. With enhanced sensitivity, the ultrasound system can utilize higher frequencies and/or broader bandwidths to provide high-resolution images at farther imaging depths while meeting power-intensity guidelines.

20 Claims, 23 Drawing Sheets

(56) References Cited

U.S. PATENT DOCUMENTS

| | | | | |
|---|---|---|---|---|
| 8,334,729 | B1 | 12/2012 | Khlat | |
| 8,864,673 | B2 | 10/2014 | Miyake | |
| 10,368,970 | B2 | 8/2019 | King | |
| 12,539,100 | B2 * | 2/2026 | Zhang | A61B 8/429 |
| 2019/0337014 | A1 * | 11/2019 | Chatain | B06B 1/20 |
| 2025/0213218 | A1 * | 7/2025 | Zhang | A61B 8/429 |
| 2025/0216526 | A1 * | 7/2025 | Zhang | G01S 7/52019 |
| 2026/0123913 | A1 | 5/2026 | Zhang et al. | |

FOREIGN PATENT DOCUMENTS

| | | | | | |
|---|---|---|---|---|---|
| CN | 119921874 | A | * | 5/2025 | |
| JP | 2004097588 | A | * | 4/2004 | |
| KR | 20170057869 | A | * | 5/2017 | A61B 8/486 |
| KR | 20170115921 | A | * | 10/2017 | G01S 15/895 |

OTHER PUBLICATIONS

Translation of CN-119921874 (Year: 2025).*
Translation of KR-20170115921 (Year: 2017).*
“Non-Final Office Action”, U.S. Appl. No. 18/400,116, Jul. 24, 2025, 10 pages.
“Restriction Requirement”, U.S. Appl. No. 18/400,116, Jun. 27, 2025, 8 pages.
“Notice of Allowance”, U.S. Appl. No. 18/400,116, Dec. 1, 2025, 9 pages.

* cited by examiner

210

102

1200

TRANSDUCER MODULE ARCHITECTURE FOR ENHANCING SENSITIVITY OF AN ULTRASOUND SYSTEM

BACKGROUND

An ultrasound system provides a non-invasive way of imaging a person's body. To produce a higher-resolution image, some ultrasound systems utilize higher frequencies and/or broader bandwidths. These higher frequencies and/or broader bandwidths, however, can pose many challenges. One such challenge is the larger amount of attenuation that these signals can experience while propagating through the human body compared to lower frequency and/or narrower bandwidth signals. This attenuation limits an imaging depth of the ultrasound system. In other words, an ultrasound system that utilizes higher frequencies and/or broader bandwidths may be unable to image areas of the human body that are farther below the surface compared to another ultrasound system that utilizes lower frequencies. This inherent tradeoff between resolution performance and imaging depth makes it challenging to design an ultrasound system that can provide high-resolution images at farther imaging depths.

SUMMARY

Systems and methods for implementing a transducer module architecture that enhances sensitivity of an ultrasound system are described. To meet cost and size constraints, an architecture of a transducer module includes a transducer element that is disposed within both a transmit path and a receive path of the ultrasound system. As such, the transducer element is utilized for both transmission and reception. To enhance sensitivity of the ultrasound system while using the transducer element for both transmission and reception, the architecture of the transducer module provides operation-specific impedance matching. Operation-specific impedance matching means that different impedances are provided for mitigating mismatch loss between a transmitter of the ultrasound system and the transducer element for transmission, and for mitigating mismatch loss between the transducer element and a receiver of the ultrasound system for reception. The impedance provided for reception can be associated with a smaller amount of attenuation (or voltage drop) compared to the impedance provided for transmission. In this way, the architecture enhances sensitivity of the ultrasound system by reducing an amount of attenuation experienced during reception compared to other ultrasound systems that utilize a same impedance for impedance matching during transmission and reception. With enhanced sensitivity, the ultrasound system can utilize higher frequencies and/or broader bandwidths to provide high-resolution images at farther imaging depths without increasing transmission power.

In some aspects, an apparatus is disclosed. The apparatus includes a transducer module of an ultrasound system. The transducer module includes a transducer element and an impedance matching circuit. The transducer element is configured to be coupled to a transmitter and a receiver of the ultrasound system. The transducer element is also configured to transmit an ultrasound transmit signal during a first time interval and receive an ultrasound receive signal during a second time interval that differs from the first time interval. The impedance matching circuit is coupled to the transducer element. The transducer module has an architecture that is configured to propagate a version of the ultrasound transmit signal that is provided by the transmitter in a manner that passes through the impedance matching circuit to the transducer element during the first time interval. The architecture is also configured to propagate a version of the ultrasound receive signal from the transducer element to the receiver in a manner that bypasses at least a portion of the impedance matching circuit during a second time interval.

In some aspects, a method for enhancing sensitivity of an ultrasound system is disclosed. The method includes propagating a version of an ultrasound transmit signal provided by a transmitter of the ultrasound system through an impedance matching circuit of a transducer module of the ultrasound system to a transducer element of the transducer module. The impedance matching circuit includes at least one series component. The method also includes transmitting the ultrasound transmit signal using the transducer element and receiving an ultrasound receive signal using the transducer element. The method further includes propagating a version of the ultrasound receive signal from the transducer element to a receiver of the ultrasound system in a manner that bypasses the at least one series component of the impedance matching circuit.

In some aspects, a transducer module of an ultrasound system is disclosed. The transducer module includes a transducer element and an impedance matching circuit. The transducer element is disposed within a shared transceiver path of the ultrasound system and is configured to transmit and receive ultrasound signals. The impedance matching circuit is coupled to the transducer element and disposed within at least a transmit path of the ultrasound system. The transducer module has an architecture that causes operation-specific impedance matching to be provided using at least the impedance matching circuit.

In some aspects, an apparatus is disclosed. The apparatus includes a transducer module of an ultrasound system. The transducer module includes a transducer element, an impedance matching circuit, and a bypass circuit. The impedance matching circuit is configured to be coupled between the transducer element and a node that is disposed within a transmit path and a receive path of the ultrasound system. The bypass circuit is coupled to the node and configured to selectively be in a first state during transmission and a second state during reception. The first state causes current to pass from the node to the transducer element through the impedance matching circuit. The second state causes the current to pass from the transducer element to the node in a manner that bypasses at least a portion of the impedance matching circuit.

In some aspects, an apparatus is disposed. The apparatus includes a transducer module of an ultrasound system. The transducer module includes a transducer element, an impedance matching circuit, and a switching circuit. The transducer element is coupled to a node that is disposed within a transmit path and a receive path of the ultrasound system. The impedance matching circuit is disposed within the transmit path and is configured to be coupled between the node and a transmitter of the ultrasound system. The switching circuit is disposed within the receive path and is configured to be coupled between the node and a receiver of the ultrasound system.

Other systems, machines, and methods to provide a transducer module architecture for enhancing sensitivity of an ultrasound system are also described. The described transducer module architectures can be applied to ultrasound systems used in medical facilities as well as other types of ultrasound systems.

BRIEF DESCRIPTION OF THE DRAWINGS

The appended drawings illustrate examples and are, therefore, exemplary embodiments and not considered to be limiting in scope.

FIG. 3-1 illustrates a first example impedance matching circuit of an ultrasound system.

FIG. 3-2 illustrates a second example impedance matching circuit of an ultrasound system.

FIG. 7-1 illustrates an example transducer module having a first architecture and coupled to an example transceiver.

FIG. 7-2 illustrates a relationship between an impedance matching circuit and a shared transceiver path in accordance with a first architecture of a transducer module.

FIG. 7-3 illustrates another relationship between an impedance matching circuit and a shared transceiver path in accordance with a first architecture of a transducer module.

FIG. 8-1 illustrates a first example implementation of a first architecture of a transducer module for enhancing sensitivity of an ultrasound system.

FIG. 8-2 illustrates a second example implementation of a first architecture of a transducer module for enhancing sensitivity of an ultrasound system.

FIG. 8-3 illustrates a third example implementation of a first architecture of a transducer module for enhancing sensitivity of an ultrasound system.

FIG. 9-1 illustrates an example transducer module having a second architecture and coupled to a first example transceiver.

FIG. 9-2 illustrates an example transducer module having a second architecture and coupled to a second example transceiver.

FIG. 10-1 illustrates a first example implementation of a second architecture of a transducer module for enhancing sensitivity of an ultrasound system.

FIG. 10-2 illustrates a second example implementation of a second architecture of a transducer module for enhancing sensitivity of an ultrasound system.

FIG. 10-3 illustrates a third example of a second architecture of a transducer module for enhancing sensitivity of an ultrasound system.

FIG. 11-1 illustrates first example frequency responses of different ultrasound systems.

FIG. 11-2 illustrates second example frequency responses of different ultrasound systems.

FIG. 11-3 illustrates third example frequency responses of different ultrasound systems.

DETAILED DESCRIPTION

An inherent tradeoff between resolution performance and imaging depth makes it challenging to design an ultrasound system that can provide high-resolution images at farther imaging depths. Some techniques can address this issue by increasing output power or concentrating energy in a particular direction to compensate for the attenuation. These types of compensation techniques, however, increase power densities. To meet guidelines promulgated by the government or industry, such as a maximum acoustic output exposure level s as determined by the Food and Drug Administration (FDA), such compensation techniques may be constrained. As such, some ultrasound systems can continue to struggle with providing high-resolution images at farther depths.

To address this challenge, systems, devices, and techniques are disclosed herein for implementing a transducer module architecture that enhances sensitivity of an ultrasound system. The techniques described herein can be applied to a transducer module that includes a transducer element disposed within both a transmit path and a receive path of the ultrasound system. To enhance sensitivity of the ultrasound system while using the transducer element for both transmission and reception, the architecture of the transducer module provides operation-specific impedance matching. Operation-specific impedance matching means that different impedances are provided for mitigating mismatch loss between a transmitter of the ultrasound system and the transducer element for transmission, and for mitigating mismatch loss between the transducer element and a receiver of the ultrasound system for reception. The impedance provided for reception can be associated with a smaller amount of attenuation (or voltage drop) compared to the impedance provided for transmission. In this way, the architecture enhances sensitivity of the ultrasound system by reducing an amount of attenuation experienced during reception compared to other ultrasound systems that utilize a same impedance for impedance matching during transmission and reception. With enhanced sensitivity, the ultrasound system can utilize higher frequencies and/or broader bandwidths and provide high-resolution images at farther imaging depths while meeting power-intensity guidelines.

Enhancing Sensitivity in an Ultrasound System

Figure 1:
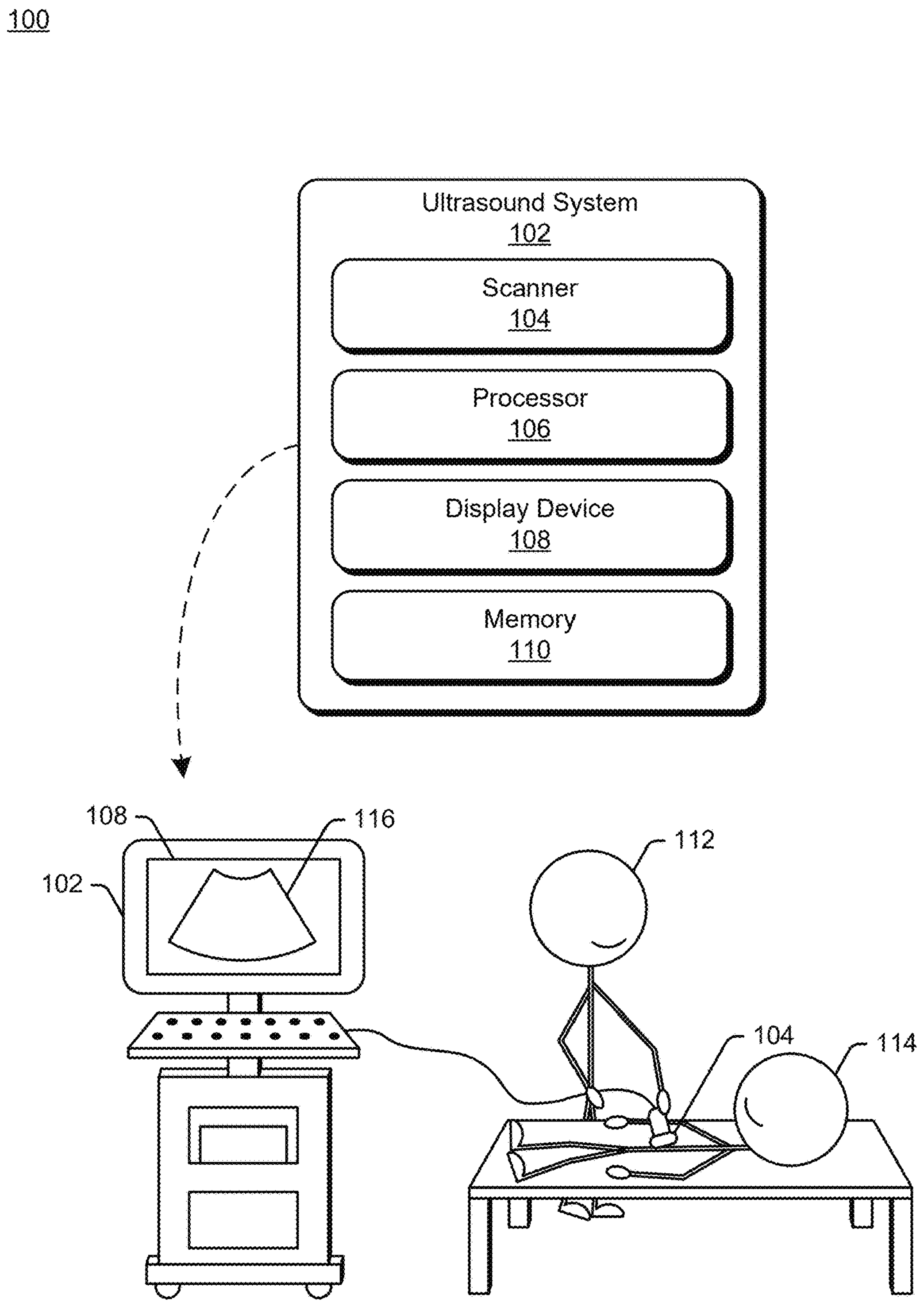
FIG. 1 illustrates an example environment for enhancing sensitivity of an ultrasound system in accordance with one or more implementations.

FIG. 1 illustrates an example environment 100 for enhancing sensitivity in an ultrasound system 102 in accordance with one or more implementations. The ultrasound system 102 (or ultrasound machine) uses ultrasound to generate data (including images) of a portion of a human body. More specifically, the ultrasound system 102 transmits and receives acoustic waves that are reflected by one or more objects (or structures) within the human body. Example objects include a part of the human body (e.g., an organ, tissue, free fluid, an anatomy part, or an abnormality) or a foreign object that is within the human body (e.g., an implant, an inanimate object, or a parasite).

Generally, the ultrasound system 102 includes at least one scanner 104, at least one processor 106, at least one display device 108, and at least one memory 110. The scanner 104 transmits and receives ultrasound signals, and is sometimes referred to as an ultrasound probe. The processor 106 is coupled to the scanner 104 and processes the reflected ultrasound signals to generate ultrasound data. The display device 108 is coupled to the processor 106 and generates an ultrasound image based on the ultrasound data. The display device 108 can include multiple display devices. For instance, a first display device can display a first ultrasound image, and a second display device can display a focused ultrasound image or a segmentation image that is generated based on the first ultrasound image.

In the example environment 100, a user 112 (e.g., a nurse, an ultrasound technician, an operator, or a sonographer)

directs the scanner 104 toward a patient 114 to non-invasively scan an object within the patient 114 for testing, diagnostic, procedural, or therapeutic reasons. The ultrasound system 102 displays an ultrasound image 116 using the display device 108. To enable the ultrasound system 102 to generate high-resolution ultrasound data (and images) at farther depths, the scanner 104 includes a transducer module with an architecture that enhances sensitivity, as further described with respect to FIG. 2.

Figure 2:
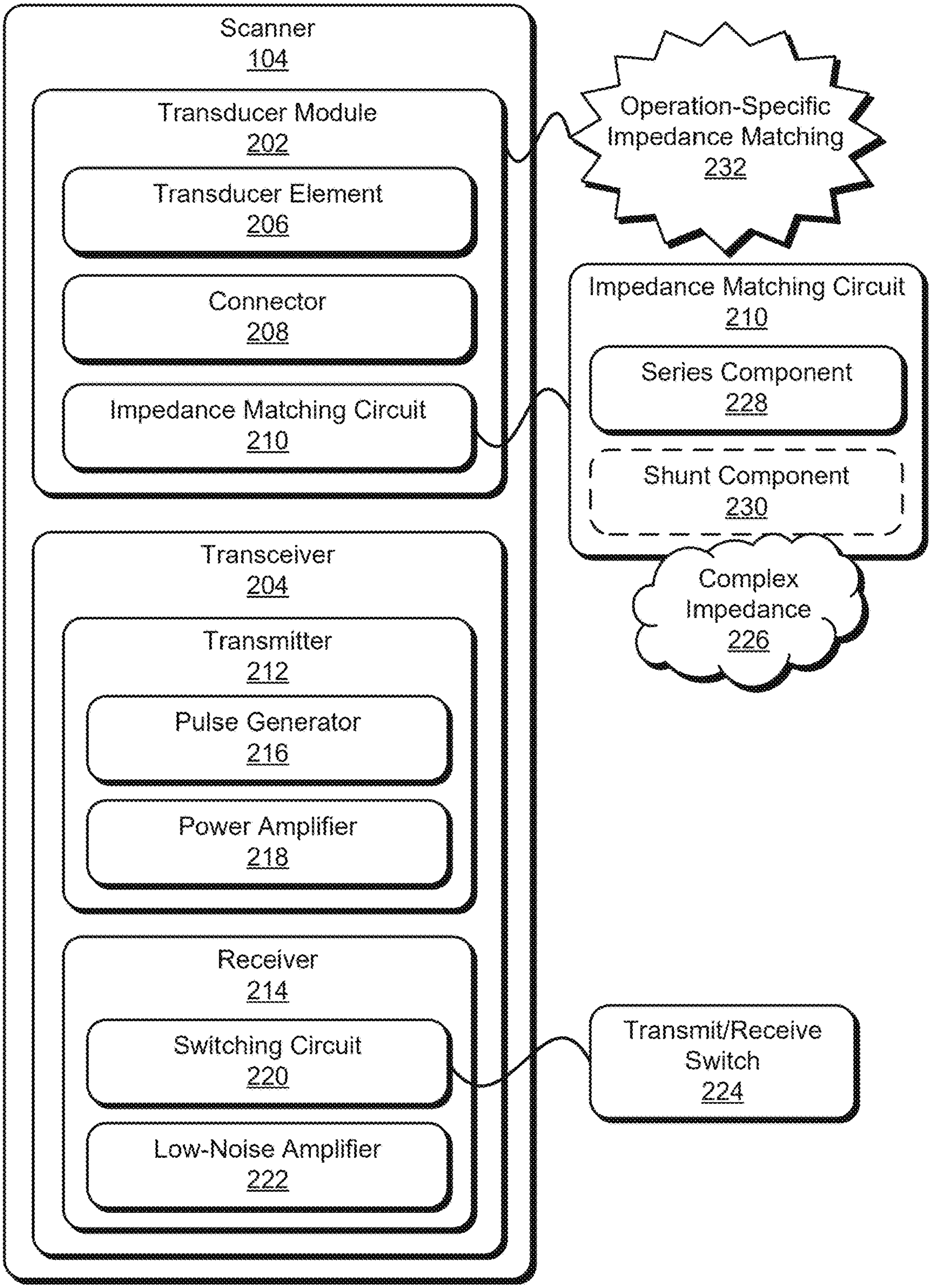
FIG. 2 illustrates example components of a scanner for enhancing sensitivity in an ultrasound system.

FIG. 2 illustrates example components of the scanner 104. In the depicted configuration, the scanner 104 includes at least one transducer module 202 and at least one transceiver 204. Although the transducer module 202 and the transceiver 204 are shown to be separate entities in FIG. 2, it is to be understood that some implementations of the ultrasound system 102 can integrate one or more components of the transceiver 204 within the transducer module 202.

The transducer module 202 includes at least one transducer element 206, at least one connector 208, and at least one impedance matching circuit 210. The components of the transducer module 202 can be packaged together as a single entity. The transducer element 206 transmits and receives ultrasound signals. In some implementations, the transducer module 202 includes multiple transducer elements 206 that are arranged in a one-dimensional or multi-dimensional array. The one or more transducer elements 206 can be implemented on an integrated circuit, as further described with respect to FIG. 4. Additionally or alternatively, the one or more transducer elements 206 can be implemented by using a layer of piezoelectric material cut, e.g., diced, to form the transducer elements, as part of a transducer stack. Using mechanical or electronic beam steering (e.g., beamforming), the one or more transducer elements 206 can scan a narrow or a wide sector of a human body.

A size, shape, and weight of the transducer module 202 can be designed for hand-held use of the scanner 104. In this way, the user 112 can easily position and angle the transducer element 206 towards a particular region of the subject 114 and move the transducer element 206 to observe different objects (or different parts of an object) within the subject 114. Utilizing the transducer element 206 for both transmission and reception can enable size, space, and/or cost constraints to be met.

The connector 208 couples the transducer element 206 to at least a portion of the transceiver 204 and/or the processor 106. In some examples described herein, the connector 208 represents any type of wired interface that passes signals between the transducer element 206 and other components of the ultrasound system 102. In some implementations, the connector 208 is implemented using a coaxial cable. Other implementations are also possible in which the connector 208 represents a wireless interface that passes signals over-the-air between the transducer element 206 and other components of the ultrasound system 102. Hence, the connector 208 can act as a coupler.

The transceiver 204 includes circuitry and/or logic for transmitting and receiving ultrasound signals via the transducer element 206. Components of the transceiver 204 can include, for example, amplifiers, phase shifters, mixers, switches, analog-to-digital converters, digital-to-analog converters, or filters for conditioning the ultrasound signals. A frequency spectrum (e.g., range of frequencies) that the transceiver 204 uses to generate the ultrasound signals can encompass frequencies greater than or equal to 20 kilohertz (kHz). In some examples, the frequency range of the transceiver 204 includes frequencies between 20 kHz and 4 gigahertz (GHz), between 2 and 20 megahertz (MHz), between 20 MHz and 2 GHz, and so forth.

The transceiver 204 includes at least one transmitter 212 and at least one receiver 214. The transmitter 212 includes at least one pulse generator 216 and at least one power amplifier (PA) 218. The pulse generator 216 generates a signal for transmission. The power amplifier 218 amplifies this signal, and the transducer element 206 transmits this amplified signal as an ultrasound transmit signal, as further described with respect to FIG. 4.

The receiver 214 includes at least one switching circuit 220 and at least one low-noise amplifier (LNA) 222. The switching circuit 220 protects the components within the receiver 214 (e.g., the low-noise amplifier 222) during transmission by isolating (or disconnecting) these components from the transmitter 212 and the transducer element 206. During reception, the switching circuit 220 connects the low-noise amplifier 222 to the transducer element 206. In some implementations, the switching circuit 220 is implemented using a transmit/receive (T/R) switch 224. The transmit/receive switch 224 can be a duplexer, a circulator, or a network of diode switches. The low-noise amplifier 222 amplifies a version of an ultrasound signal that is received using the transducer element 206.

The impedance matching circuit 210 can mitigate mismatch loss for transmission and in some cases reception. More specifically, the impedance matching circuit 210 has a complex impedance 226 that can decrease signal reflection (e.g., increase power transfer) between the transducer element 206 and the transceiver 204. Generally speaking, the complex impedance 226 of the impedance matching circuit 210 can be a real impedance, an imaginary impedance (e.g., a reactance), or some combination thereof. In the depicted configuration, the impedance matching circuit 210 includes at least one series component 228. The series component 228 is coupled between an input and an output of the impedance matching circuit 210 such that a signal presented at the input propagates through the series component 228 to the output.

Optionally, the impedance matching circuit 210 also includes at least one shunt component 230 to realize a particular complex impedance 226 for impedance matching. The shunt component 230 has one terminal coupled between the input and the output and another terminal coupled to a ground. In some implementations, the series component 228 and/or the shunt component 230 form a portion of a network, such as an L-network, a T-network, or a pi-network. The series component 228 and/or the shunt component 230 can be implemented using a lumped element (e.g., an inductor, a capacitor, or a resistor), a distributed element (e.g., a stub or a quarter-wave transformer), or some combination thereof. Example implementations of the impedance matching circuit 210 are further described with respect to FIGS. 3-1 and 3-2.

Figures 1, 3:
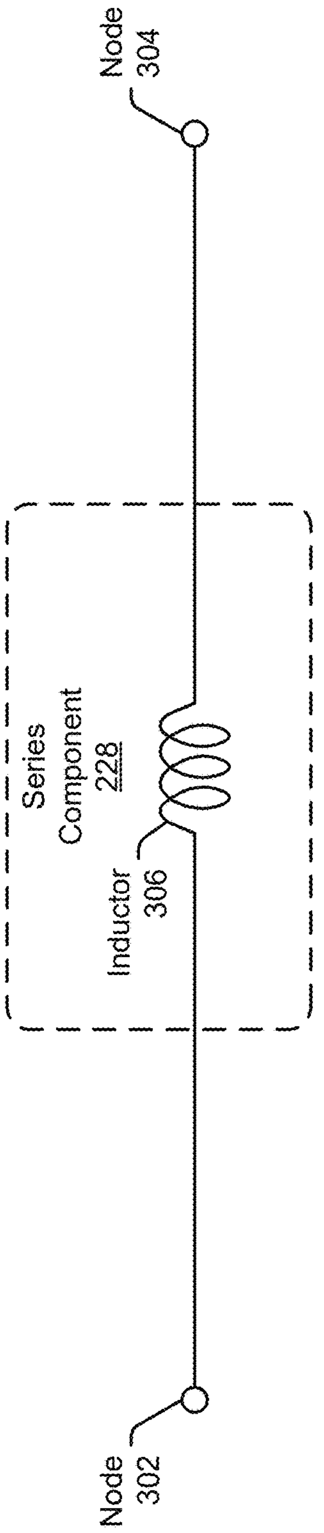
Figures 2, 3:
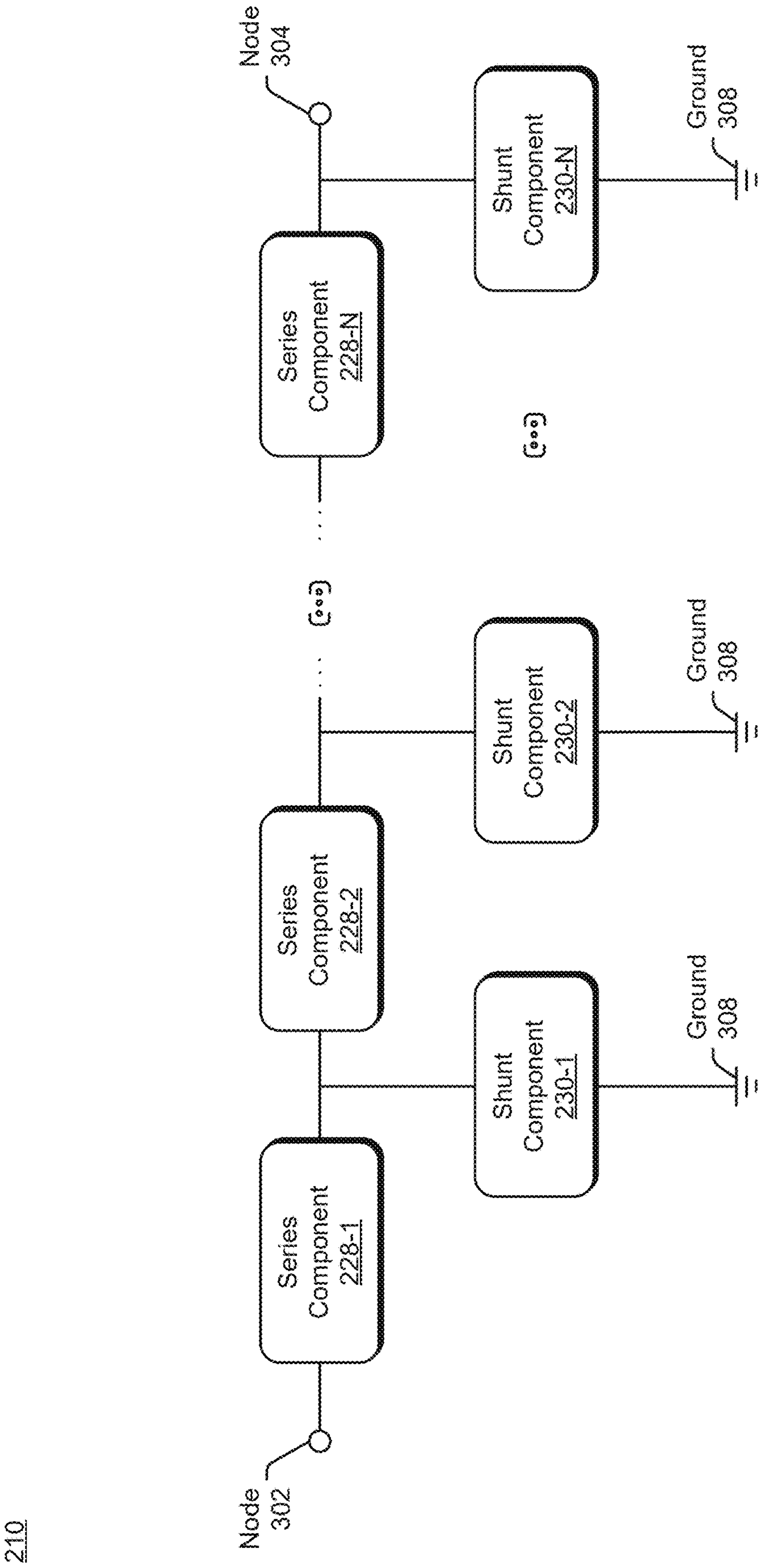

FIG. 3-1 illustrates an example implementation of the impedance matching circuit 210. In the depicted configuration, the impedance matching circuit 210 includes a first node 302 and a second node 304. Each of the nodes 302 and 304 can be coupled to a source impedance or a load impedance depending on an operation of the ultrasound system 102. In other words, the first and second nodes 302 and 304 can each represent an input node or an output node depending on whether the ultrasound system 102 is transmitting or receiving.

The impedance matching circuit 210 also includes a series component 228, which is coupled between the nodes 302 and 304. In this example, the series component 228 is implemented using an inductor 306. The inductor 306 can be a single large inductor or multiple smaller inductors. In general, the series component 228 can be implemented using any type of lumped or distributed element as explained above. The impedance matching circuit 210 can be implemented using a single series component 228, as shown in FIG. 3-1, or using multiple series components 228. In some implementations, the impedance matching circuit 210 includes one or more shunt components 230 along with the series component 228, as further described with respect to FIG. 3-2.

FIG. 3-2 illustrates another example implementation of the impedance matching circuit 210. In the depicted configuration, the impedance matching circuit 210 includes multiple series components 228-1, 228-2 . . . 228-N, where N represents a positive integer. The series components 228-1 to 228-N are coupled, in series, between the nodes 302 and 304. More specifically, the series component 228-1 is coupled between the node 302 and the series component 228-2. The series component 228-2 is coupled between the series component 228-1 and the series component 228-N. The series component 228-N is coupled between the series component 228-2 and the node 304.

The impedance matching circuit 210 can optionally include one or more shunt components 230. In this example, the impedance matching circuit 210 includes shunt components 230-1, 230-2 . . . 230-N. The shunt component 230-1 is coupled between a ground 308 and a node that is between the series components 228-1 and 228-2. The shunt component 230-2 is coupled between the ground 308 and another node that is between the series components 228-2 and 228-N. The shunt component 230-N is coupled between the ground 308 and the node 304. Generally speaking, the quantity of series components 228 and the quantity of shunt components 230 can be similar (as shown in FIG. 3-2) or different. As explained above, there are a variety of different types of networks that can be used to implement the impedance matching circuit 210 in addition to the network shown in FIG. 3-2.

Returning to FIG. 2, the complex impedance 226 of the impedance matching circuit 210 can be associated with a voltage drop across the series component 228. To enhance sensitivity of the ultrasound system 102 in situations in which the transducer element 206 supports both transmission and reception, the architecture of the transducer module 202 provides operation-specific impedance matching 232. Operation-specific impedance matching 232 means that different impedances are provided during transmission and reception for impedance matching (e.g., for mitigating mismatch loss). For example, a first impedance is provided between the transmitter 212 and the transducer element 206 for transmission. A second impedance is provided between the transducer element 206 and the receiver 214 for reception. The first impedance is different than the second impedance. In some cases, the first impedance is significantly larger in magnitude compared to the second impedance. The second impedance can also be approximately equal to zero in some example implementations.

With operation-specific impedance matching 232, at least a portion of the impedance matching circuit 210 (and in some cases an entirety of the impedance matching circuit 210) is bypassed for reception. More specifically, the architecture of the transducer module 202 enables a version of an ultrasound transmit signal to propagate through the impedance matching circuit 210 while enabling a version of an ultrasound receive signal to bypass at least one series component 228 of the impedance matching circuit 210 (e.g., one series component 228, multiple series components 228, or all series components 228 of the impedance matching circuit 210). By bypassing at least a portion of the impedance matching circuit 210, the architecture avoids the attenuation (e.g., voltage drop) associated with this portion of the impedance matching circuit 210, which enhances sensitivity of the ultrasound system 102. In some examples, the sensitivity of the ultrasound system 102 can be increased by approximately 2 decibels (dB) or more (e.g., by 3, 4, 6, 10 dB or more) compared to other ultrasound systems that provide a same impedance for impedance matching during transmission and reception. With enhanced sensitivity, the ultrasound system 102 can utilize higher frequencies and/or broader bandwidths to provide high-resolution images at farther imaging depths without increasing power densities.

Operation-specific impedance matching 232 also provides additional flexibility in tailoring a frequency response of the ultrasound system 102 for reception. For example, an architecture of the transducer module 202 can be designed in a manner that increases sensitivity within a particular portion of a frequency band of the ultrasound system 102 (e.g., within a lower portion or a higher portion of the frequency band). Additionally or alternatively, the architecture of the transducer module 202 can be designed in a manner that enables the ultrasound system 102 to realize a particular bandwidth. This aspect of operation-specific impedance matching 232 is further described with respect to FIGS. 11-1 to 11-3. An operation of the scanner 104 is further described with respect to FIG. 4.

Figure 4:
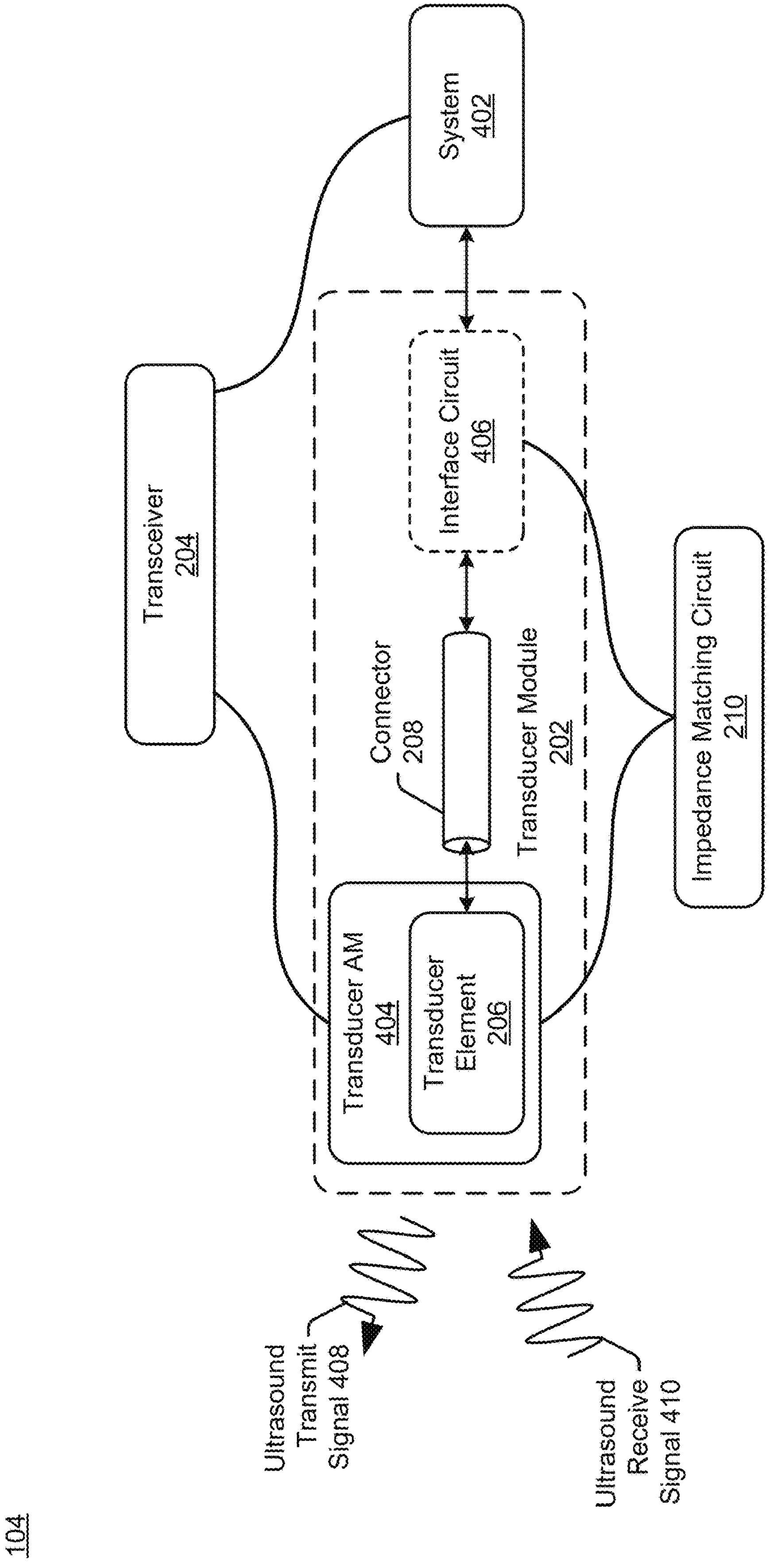
FIG. 4 illustrates an example implementation of a scanner.

FIG. 4 illustrates an example implementation of the scanner 104. In the depicted configuration, the scanner 104 includes at least one system 402 and at least one transducer array module 404 (transducer AM 404). In some implementations, the system 402 includes at least one integrated circuit, which can implement components of the transceiver 204.

Figures 1, 10:
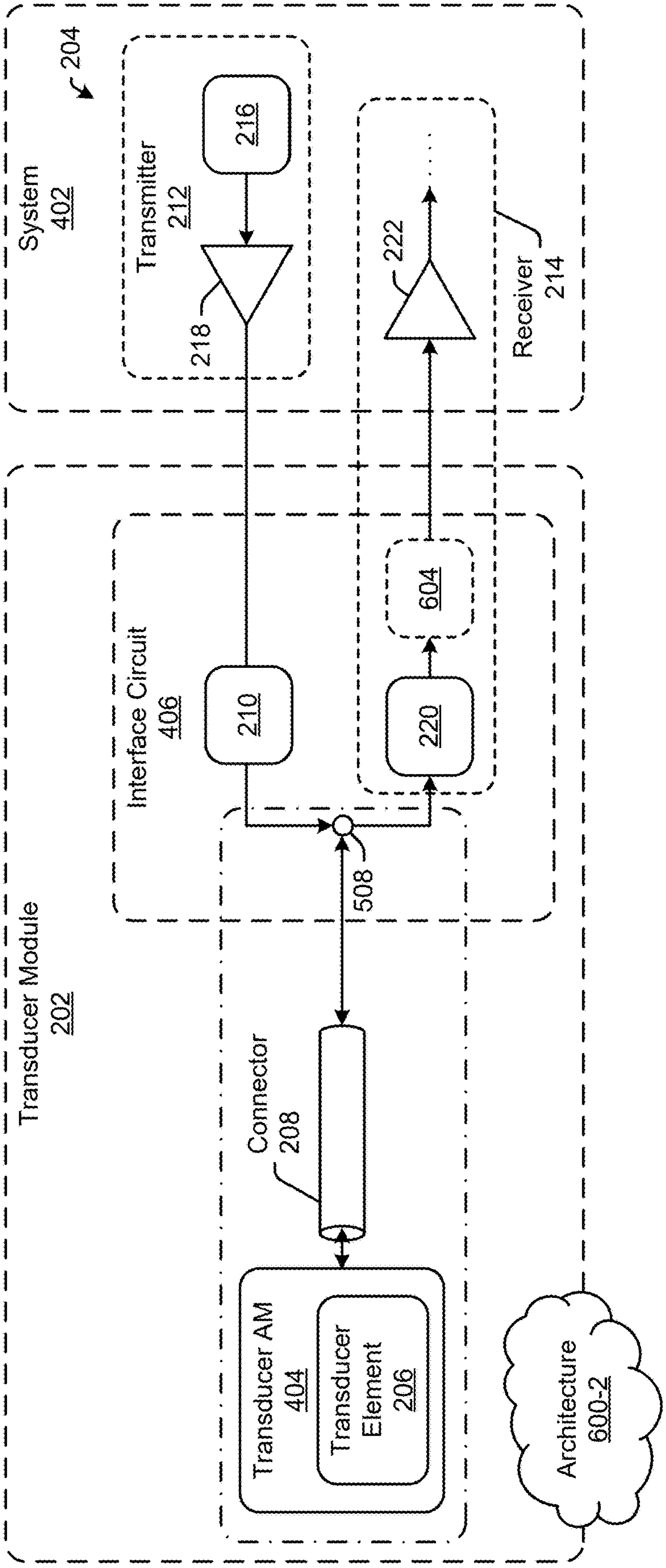
Figures 2, 10:
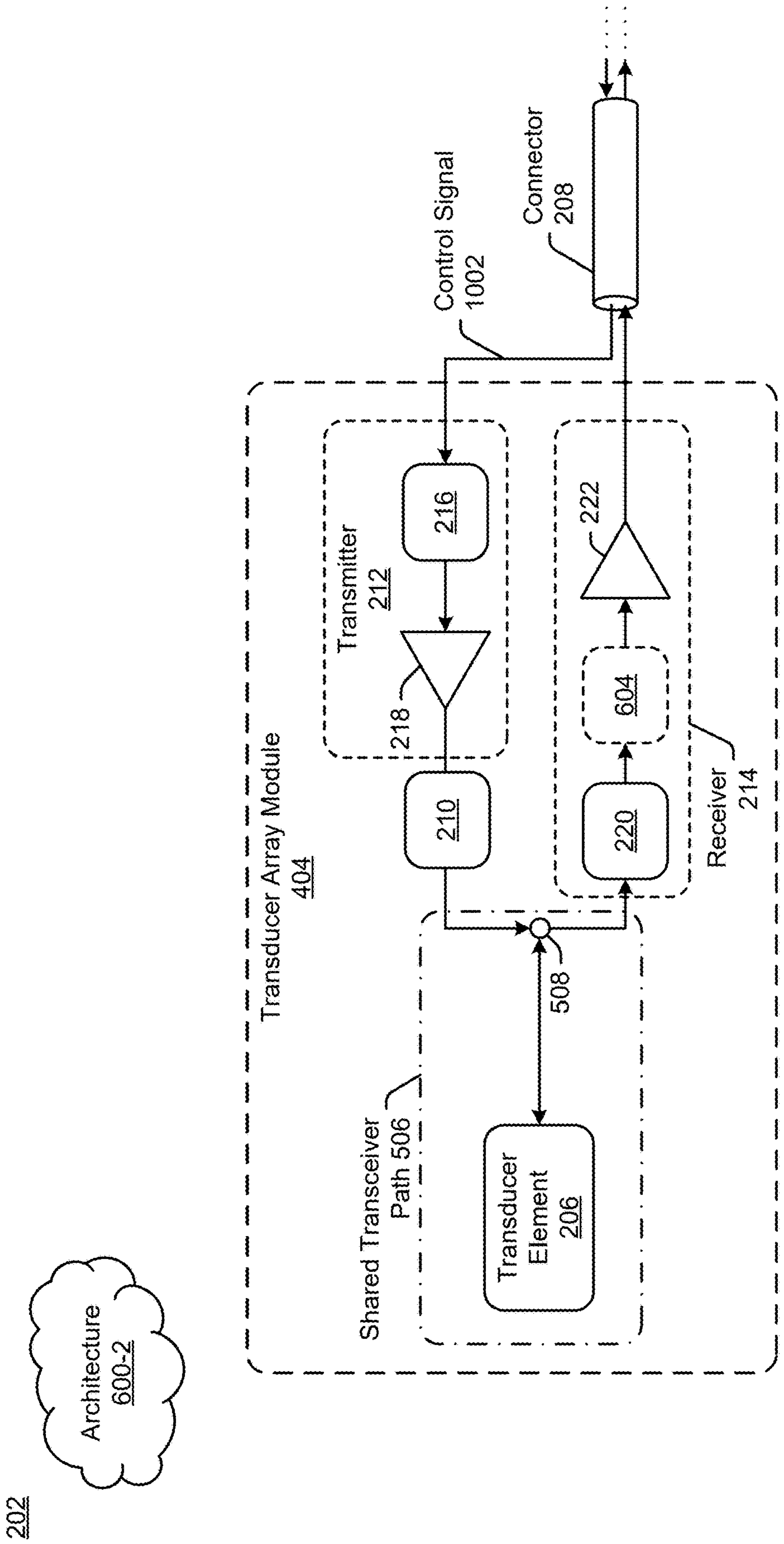
Figures 3, 10:
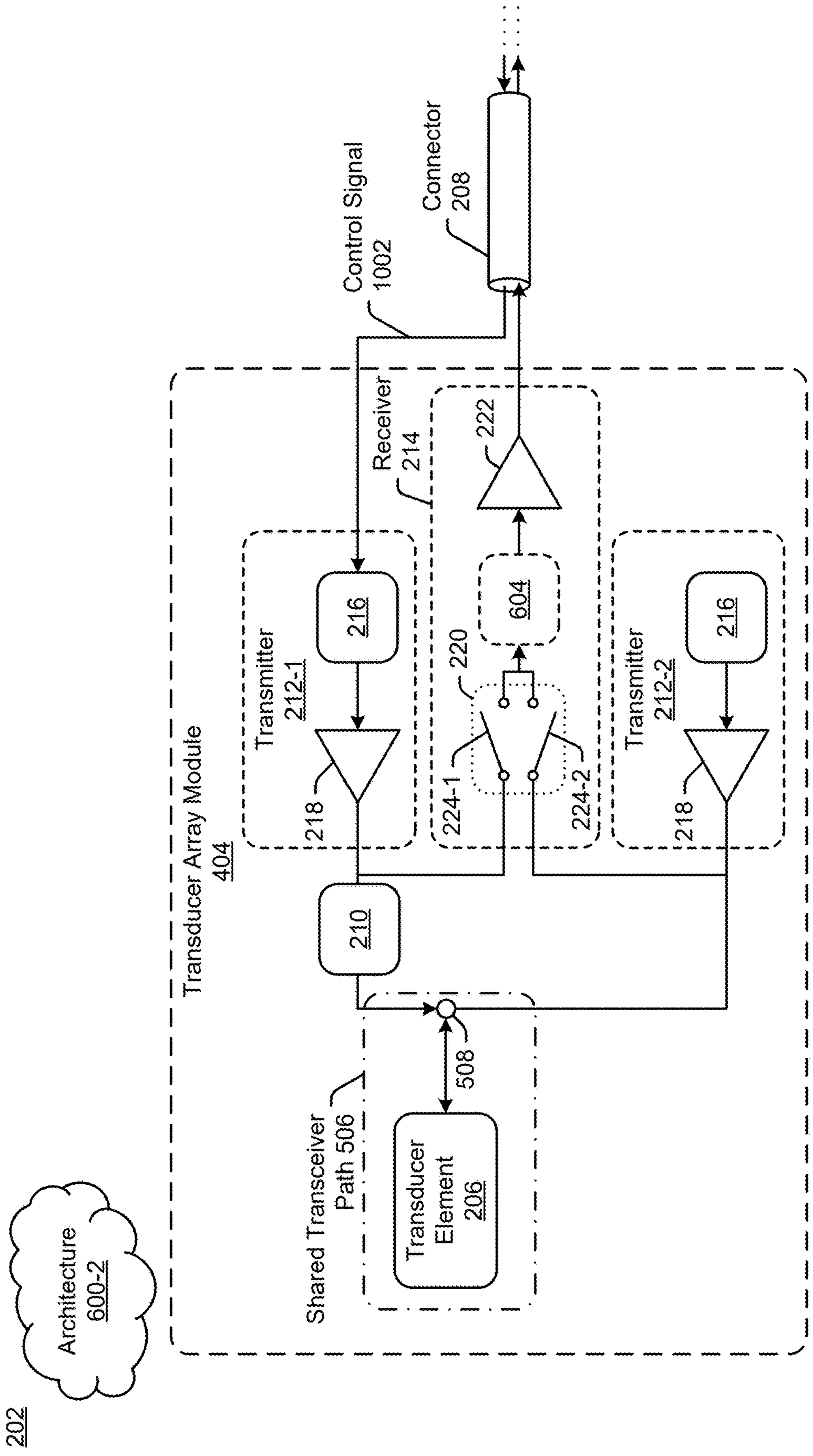

The transducer array module 404 includes acoustic and/or electronic components, which can be packaged together. The transducer array module 404 includes at least one transducer element 206. In various implementations, the transducer array module 404 can include a single transducer element 206 or multiple transducer elements 206 that form an array. In FIGS. 10-2 and 10-3, the transducer array module 404 also includes a front-end portion of the transceiver 204. The front-end portion of the transceiver 204 can be implemented on an integrated circuit in some implementations.

The scanner 104 can optionally include an interface circuit 406. The interface circuit 406 is coupled between the transducer array module 404 and the system 402. In some implementations, the interface circuit 406 is implemented as an integrated circuit. Although not explicitly shown, the system 402 can be coupled to other components of the ultrasound system 102, such as the processor 106 and/or the display device 108.

The scanner 104 also includes the transducer module 202, the transceiver 204, the transducer element 206, the connector 208, and the impedance matching circuit 210, as described with respect to FIG. 2. The transducer module 202 includes the transducer array module 404, the connector 208, and the interface circuit 406 (if implemented). The connector 208 couples the transducer array module 404 to the interface circuit 406 and/or the system 402. The impedance matching circuit 210 and the transceiver 204 can be implemented within or across various integrated circuits, as further described below.

In a first implementation, the impedance matching circuit 210 is implemented within the interface circuit 406, and the transceiver 204 is implemented within the system 402. Examples of this first implementation are further described with respect to FIGS. 7-1, 8-1, 8-2, 8-3, 9-1, 9-2, and 10-1.

In a second implementation, the impedance matching circuit 210 is implemented within the transducer array module 404, and at least a portion of the transceiver 204 is implemented within the transducer array module 404. In some cases, the transceiver 204 includes a first set of components that are implemented within the transducer array module 404 and a second set of components that are implemented within the system 402. In the second implementation, the transducer module 202 can be implemented without the interface circuit 406. Examples of this type second implementation are further described with respect to FIGS. 10-2 and 10-3.

The impedance matching circuit 210 is generally described as being implemented within various circuits, including integrated circuits (ICs). Implementations are also possible in which one or more components of the impedance matching circuit 210 are implemented off-chip and coupled to components of a circuit or an integrated circuit.

In aspects, the scanner 104 represents a half-duplex system. This means that the scanner 104 transmits and receives ultrasound signals at different times. During transmission, the transmitter 212 of the transceiver 204 generates and amplifies a transmit signal. An architecture of the transducer module 202 passes this transmit signal from the transmitter 212 to the impedance matching circuit 210. The transmit signal propagates (e.g., passes) through the impedance matching circuit 210 to the transducer element 206. The transducer element 206 transmits this signal as an ultrasound transmit signal 408.

During reception, the transducer element 206 receives an ultrasound receive signal 410. The ultrasound receive signal 410 can represent a version of the ultrasound transmit signal 408 that is reflected by an object within the subject 114. The transducer module 202 passes a version of the ultrasound receive signal 410 to the receiver 214 of the transceiver 204. In accordance with operation-specific impedance matching 232, the architecture of the transducer module 202 causes the ultrasound receive signal 410 to bypass at least a portion of the impedance matching circuit 210 to enhance sensitivity of the ultrasound system 102, as further described with respect to FIG. 6. Components of the scanner 104 can be described as being disposed within a transmit path, a receive path, or a shared transceiver path of the ultrasound system 102, as further described with respect to FIG. 5.

Figure 5:
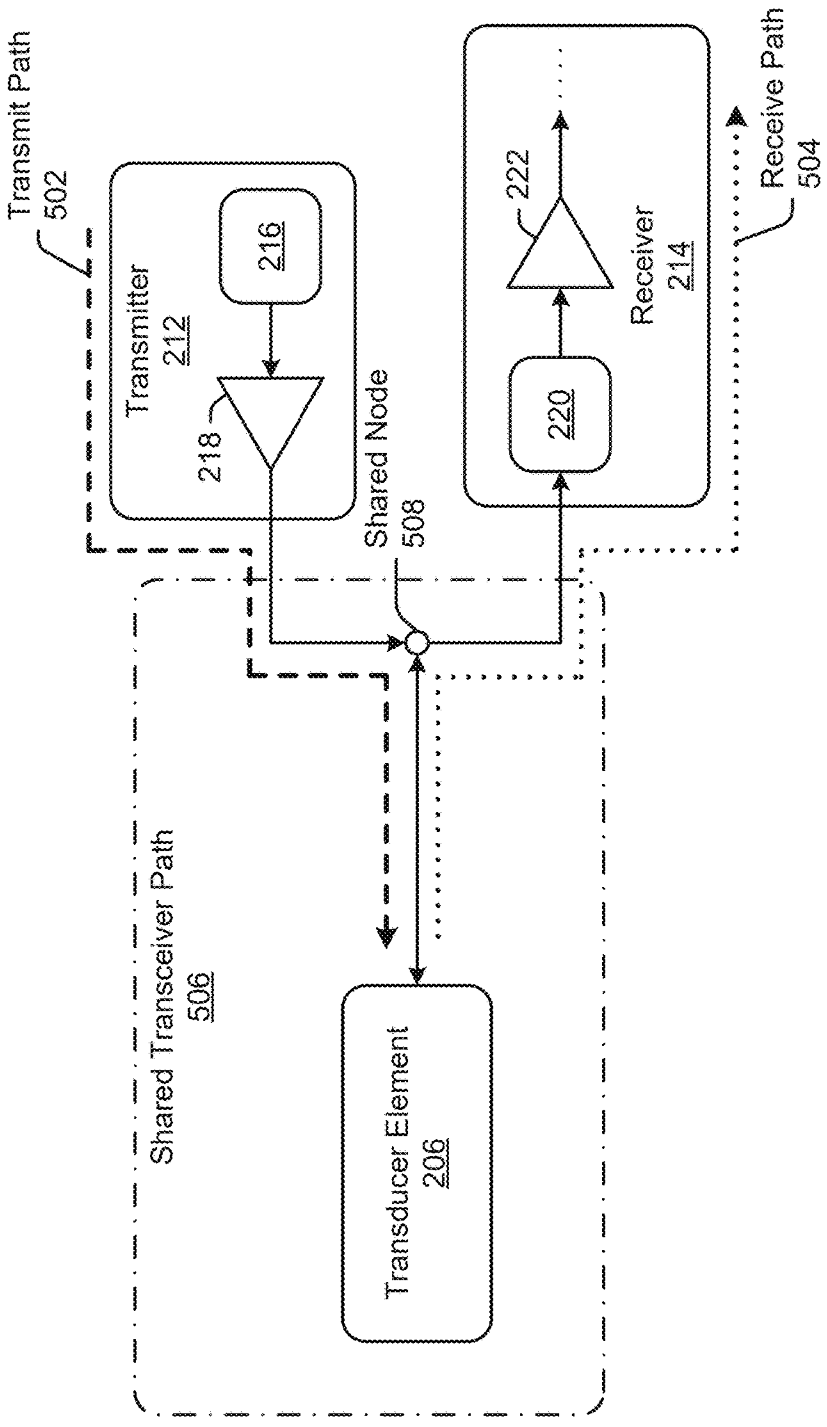
FIG. 5 illustrates example paths associated with an ultrasound system.

FIG. 5 illustrates example paths associated with the ultrasound system 102. In the depicted configuration, the ultrasound system 102 is shown to include at least one transmit path 502, at least one receive path 504, and at least one shared transceiver path 506. Components that are disposed within the transmit path 502 generate or condition signals associated with transmission. Components that are disposed within the receive path 504 generate or condition signals associated with reception. Components that are disposed within the shared transceiver path 506 condition signals for both transmission and reception. As shown in FIG. 5, the transmitter 212 is disposed within the transmit path 502, and the receiver 214 is disposed within the receive path 504.

The shared transceiver path 506 represents a common path that is shared by both the transmit path 502 and the receive path 504. In other words, the shared transceiver path 506 includes a portion of both the transmit path 502 and the receive path 504. The shared transceiver path 506 can enable a design of the scanner 104 to readily meet size and/or cost constraints as it allows components, such as the transducer element 206, to be utilized for both transmission and reception.

The shared transceiver path 506 can distinguish an ultrasound system 102 from other types of systems, such as a radar system or a full-duplex system. Some radar systems, for instance, may be designed with less strict size and/or cost constraints compared to the ultrasound system 102. These more relaxed constraints can enable the design of the radar systems to have separate or dedicated antenna elements for transmission and reception. As such, transmit and receive paths of the radar system can be distinct and separate. Many full-duplex systems that transmit and receive signals during a same time interval can also be implemented with distinct and separate transmit and receive paths.

In contrast to some radar systems and full-duplex systems, the transmit path 502 and the receive path 504 of the ultrasound system 102 share common components along the shared transceiver path 506. This is illustrated with a portion of the dashed line of the transmit path 502 and a portion of the dotted line of the receive path 504 being contained within the dotted-dashed lines of the shared transceiver path 506.

The transmitter 212 and the receiver 214 are coupled together at a shared node 508, which is disposed within the shared transceiver path 506. The transducer element 206 is also disposed within the shared transceiver path 506 and is coupled to the shared node 508. In this way, signals for transmission can pass from the transmitter 212 to the transducer element 206 through the shared node 508. Also, signals for reception can pass from the transducer element 206 to the receiver 214 through the shared node 508.

The switching circuit 220 of the receiver 214 can be in different states to control signal propagation based on an operation of the ultrasound system 102. For transmission, the switching circuit 220 isolates (e.g., disconnects) the low-noise amplifier 222 from the shared node 508. This enables a signal (e.g., an electrical current) to propagate from the transmitter 212 to the transducer element 206 along the transmit path 502. For reception, the switching circuit 220 connects the low-noise amplifier 222 to the shared node 508 and enables a signal to propagate from the transducer element 206 to the low-noise amplifier 222 along the receive path 504.

Although not explicitly shown in FIG. 5, the impedance matching circuit 210 is at least disposed within the transmit path 502. In some implementations, a portion of the impedance matching circuit 210 is also disposed within the receive path 504. In other implementations, the impedance matching circuit 210 is not disposed within the receive path 504.

For simplicity, the ultrasound system 102 is shown to include a single transmitter 212, a single receiver 214, and a single transducer element 206, which are disposed within a single transmit path 502, a single receive path 504, and a single shared transceiver path 506, respectively. Some implementations of the ultrasound system 102, however, can include multiple transducer elements 206, multiple transmitters 212, and multiple receivers 214. In this case, the multiple transducer elements 206 can be coupled to respective transmitters 212 and respective receivers 214. The multiple transmitters 212 can be disposed within respective transmit paths 502, and the multiple receivers 214 can be disposed within respective receive paths 504. Also, the multiple transducer elements 206 can be disposed within respective shared transceiver paths 506.

Generally speaking, the transducer module 202 includes at least a portion of the shared transceiver path 506. The transducer module 202 can optionally include portions of the transmit path 502 and/or the receive path 504 that are separate from the shared transceiver path 506. Example architectures of the transducer module 202 for enhancing sensitivity are further described with respect to FIG. 6.

Figure 6:
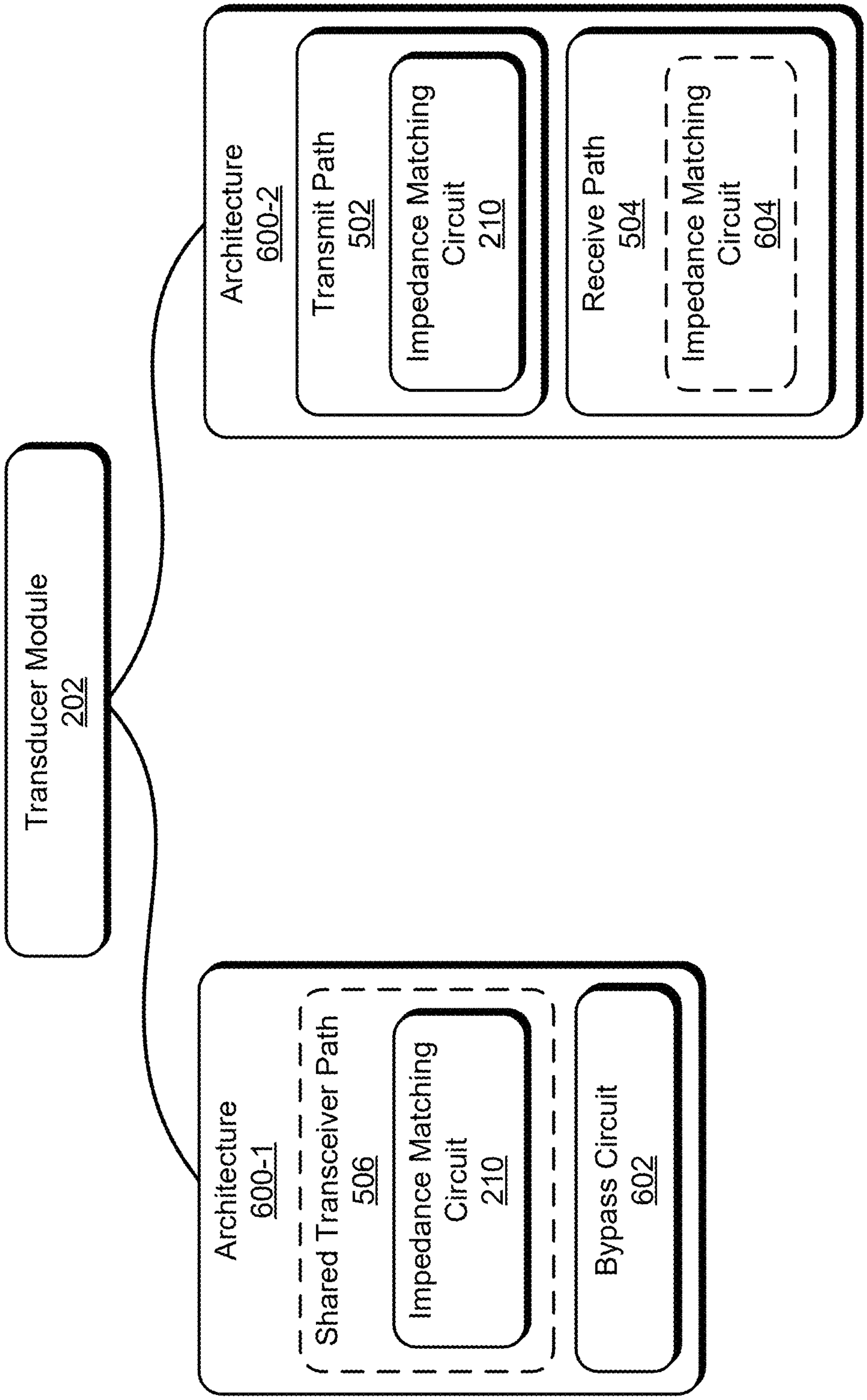
FIG. 6 illustrates example architectures of a transducer module for enhancing sensitivity in an ultrasound system.

FIG. 6 illustrates example architectures 600-1 and 600-2 of the transducer module 202. These architectures 600-1 and 600-2 enhance sensitivity in the ultrasound system 102. In general, the architectures 600-1 and 600-2 enable aspects of operation-specific impedance matching 232. More specifically, the architectures 600-1 and 600-2 provide different ways of bypassing at least a portion of the impedance matching circuit 210 (e.g., bypassing at least one series component 228 of the impedance matching circuit 210) during reception.

In a first architecture 600-1, the impedance matching circuit 210 is coupled between the transducer element 206 and the shared node 508. Optionally, the impedance matching circuit 210 can include one or more components that are disposed within the shared transceiver path 506. The transducer module 202 also includes a bypass circuit 602, which is coupled across two nodes associated with the impedance matching circuit 210. The bypass circuit 602 enables different impedances between the two nodes to be presented for transmission and reception. More specifically, the bypass circuit 602 causes a voltage drop across the two nodes to be smaller for reception compared to transmission. Examples of the first architecture 600-1 are further described with respect to FIGS. 7-1 to 8-3.

In a second architecture 600-2, the impedance matching circuit 210 is disposed within the transmit path 502 and is not disposed within the receive path 504. In other words, the shared node 508 is positioned between the transducer element 206 and the impedance matching circuit 210 such that the impedance matching circuit 210 is bypassed completely during reception. Optionally, another impedance matching circuit 604 can be disposed within the receive path 504. In this case, the other impedance matching circuit 604 provides impedance matching for reception. Examples of the second architecture 600-2 are further described with respect to FIGS. 9-1 to 10-3. Although not explicitly shown, the first architecture 600-1 can also optionally include the other impedance matching circuit 604 implemented within the receive path 504.

First Architecture for Enhancing Sensitivity

Figures 1, 7:
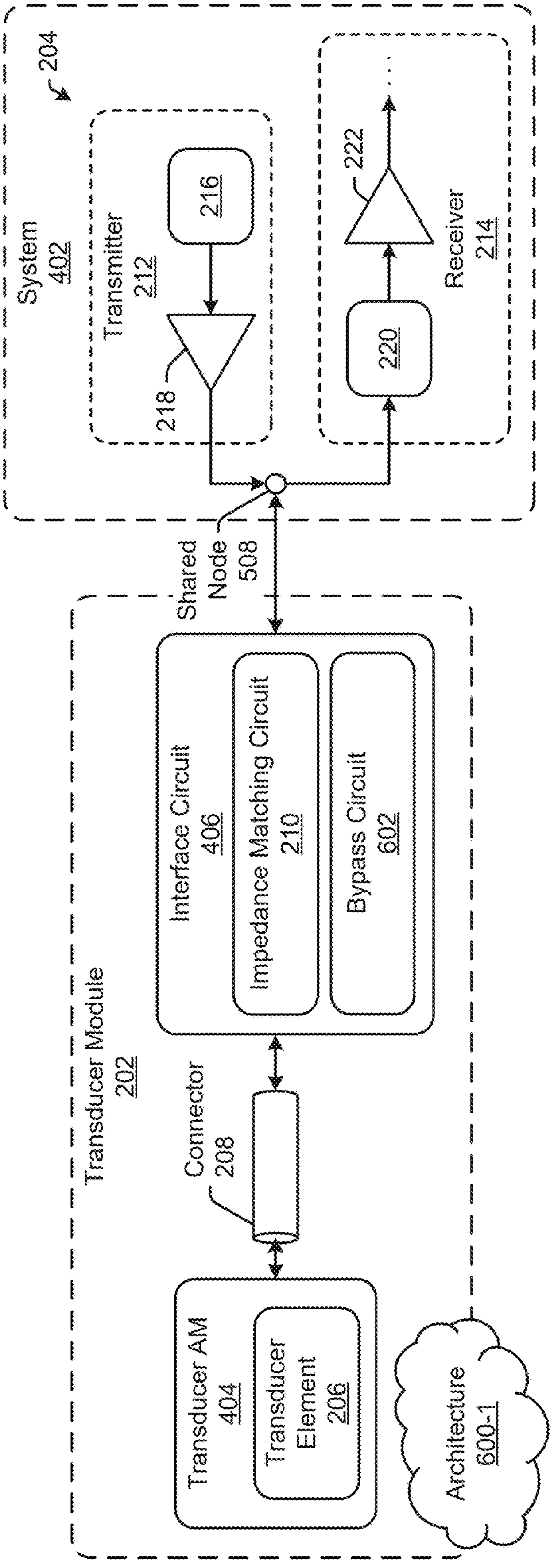
Figures 2, 7:
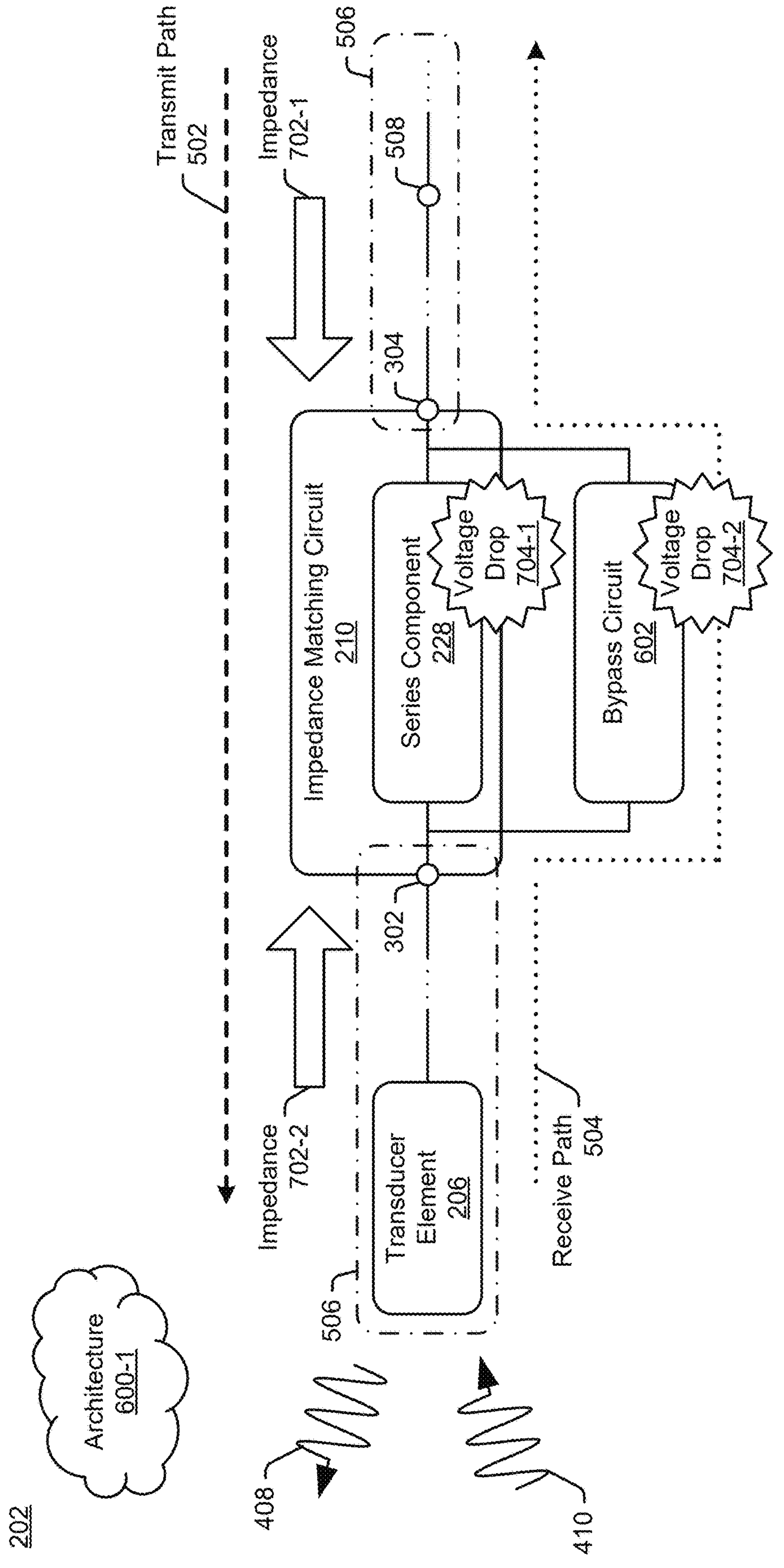
Figures 3, 7:
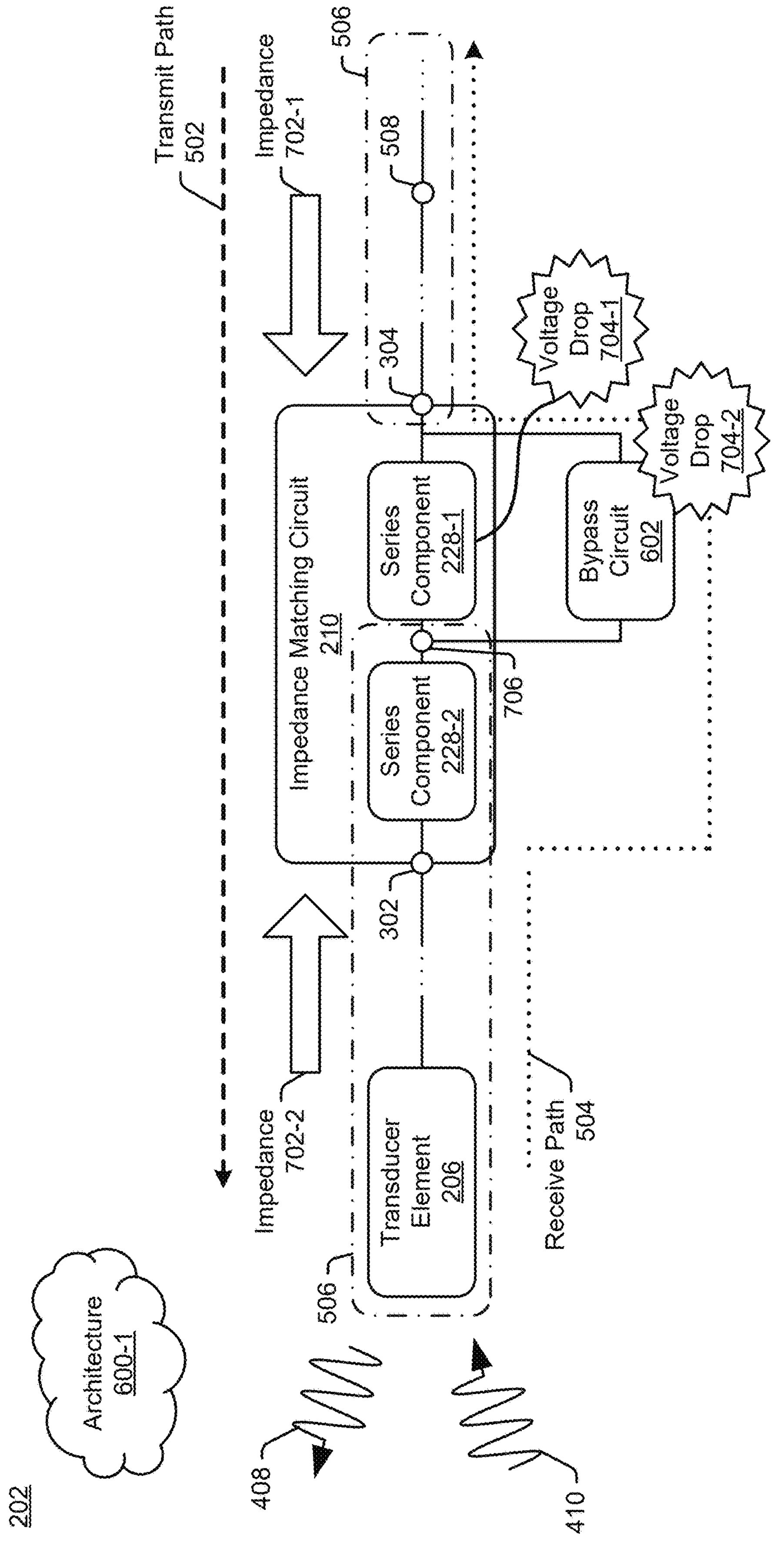

FIG. 7-1 illustrates an example transducer module 202 having the first architecture 600-1 and coupled to an example transceiver 204. In the depicted configuration, the transducer module 202 includes the transducer array module 404, the connector 208, and the interface circuit 406. The impedance matching circuit 210 and the bypass circuit 602 are implemented within the interface circuit 406. The transducer module 202 is coupled to the system 402 at the shared node 508. The transceiver 204 is implemented within the system 402. In other words, the system 402 includes the transmitter 212 and the receiver 214.

In accordance with the first architecture 600-1, the impedance matching circuit 210 is coupled between the transducer element 206 and the shared node 508. The bypass circuit 602 is also coupled between the transducer element 206 and the shared node 508. More specifically, the bypass circuit 602 is coupled between two nodes associated with the impedance matching circuit 210, as further described with respect to FIG. 7-2.

FIG. 7-2 illustrates a relationship between the impedance matching circuit 210 and the shared transceiver path 506 in accordance with the first architecture 600-1 of the transducer module 202. In the depicted configuration, the impedance matching circuit 210 includes the nodes 302 and 304 and a series component 228 having terminals respectively coupled to the nodes 302 and 304. Terminals of the bypass circuit 602 are also respectively coupled to the nodes 302 and 304.

The shared transceiver path 506 includes the transducer element 206, the shared node 508, and the nodes 302 and 304 associated with the impedance matching circuit 210. This means that signals associated with transmission and reception pass through these elements. With the architecture 600-1 and the operation of the bypass circuit 602, the series component 228 is disposed within the transmit path 502, and the bypass circuit 602 is disposed within the receive path 504. The bypass circuit 602 can be in different states to control the flow of current, as further described below.

During transmission, a signal associated with transmission flows through elements associated with the transmit path 502 and the shared transceiver path 506. Consider, for instance, that the transmitter 212 provides a version of the ultrasound transmit signal 408 at the shared node 508. The signal propagates from the shared node 508 to the node 304. The bypass circuit 602 is in a first state (or an open state), which causes the bypass circuit 602 to behave as an open circuit by presenting an impedance across the nodes 302 and 304 that is significantly larger than the impedance presented by the series component 228. This open-circuit behavior causes electrical current to propagate through the series component 228 during transmission. As such, the signal propagates from the node 304 to the node 302 through the series component 228 instead of through the bypass circuit 602. The signal also propagates from the node 302 to the transducer element 206. The transducer element 206 transmits the signal as the ultrasound transmit signal 408.

During reception, a signal associated with reception flows through elements associated with the receive path 504 and the shared transceiver path 506. Consider, for instance, that the transducer element 206 receives the ultrasound receive signal 410. The ultrasound receive signal 410 (or a version thereof) propagates from the transducer element 206 to the node 302. The bypass circuit 602 is in a second state (or a closed state), which causes the bypass circuit 602 to behave as a short circuit by presenting an impedance across the nodes 302 and 304 that is significantly smaller than the impedance presented by the series component 228. This short-circuit behavior causes electrical current to propagate through the bypass circuit 602 thereby bypassing the series component 228 during reception. As such, the signal propagates from the node 302 to the node 304 through the bypass circuit 602 instead of through the series component 228. The version of the ultrasound receive signal 410 can further pass from the shared node 508 to the receiver 214 (not shown).

The different states of the bypass circuit 602 cause different impedances 702-1 and 702-2 to be presented between the nodes 302 and 304. During transmission, a first impedance 702-1 between the nodes 302 and 304 is substantially equal to the impedance of the series component 228. The impedance of the series component 228 is associated with a first voltage drop 704-1. During reception, a second impedance 702-2 between the nodes 302 and 304 is substantially equal to the impedance of the bypass circuit 602, which behaves as a short circuit. This means that a magnitude of the second impedance 702-2 is significantly less than a magnitude of the first impedance 702-1 and is approximately equal to zero. The second impedance 702-2 can also be associated with a second voltage drop 704-2. Because the magnitude of the second impedance 702-2 is significantly less than the magnitude of the first impedance 702-1, the second voltage drop 704-2 is also significantly less than the first voltage drop 704-1. In this way, the architecture 600-1 enables different impedances to be presented between the nodes 302 and 304 during transmission and reception such that a voltage drop across the nodes 302 and 304 is less during reception compared to transmission. In this way, the architecture 600-1 enhances sensitivity of the ultrasound system 102 compared to other ultrasound systems that do not include the bypass circuit 602 and enable operation-specific impedance matching 232.

In FIG. 7-2, the impedance matching circuit 210 includes a single series component 228 between the nodes 302 and 304. Other implementations are also possible such that the impedance matching circuit 210 includes at least one additional series component 228 coupled between the nodes 302 and 304, at least one shunt component having a terminal indirectly or directly coupled to the nodes 302 and 304, or some combination thereof. An example implementation in which the impedance matching circuit 210 includes two series components 228 is further described with respect to FIG. 7-3.

FIG. 7-3 illustrates another relationship between the impedance matching circuit 210 and the shared transceiver path 506 in accordance with the first architecture 600-1 of the transducer module 202. In the depicted configuration, the impedance matching circuit 210 includes the nodes 302, 304, and 706. The impedance matching circuit 210 also includes two series components 228-1 and 228-2. The first series component 228-1 is coupled between the nodes 706 and 304. The second series component 228-2 is coupled between the nodes 302 and 706. Terminals of the bypass circuit 602 are respectively coupled to the nodes 706 and 304. The bypass circuit 602 can operate in a similar manner as described above with respect to the bypass circuit 602 of FIG. 7-2.

The shared transceiver path 506 includes the transducer element 206, the shared node 508, the nodes 302, 304, and 706 associated with the impedance matching circuit 210, and the series component 228-2. This means that signals associated with transmission and reception pass through these elements. With the architecture 600-1 and the operation of the bypass circuit 602, the series component 228-1 is disposed within the transmit path 502 and is not disposed within the receive path 504.

The different states of the bypass circuit 602 cause different impedances 702-1 and 702-2 to be presented between the nodes 706 and 304. During transmission, the first impedance 702-1 between the nodes 706 and 304 is substantially equal to the impedance of the first series component 228-1. The impedance of the first series component 228-1 is associated with the first voltage drop 704-1. During reception, the second impedance 702-2 between the nodes 706 and 304 is substantially equal to the impedance of the bypass circuit 602, which behaves as a short circuit. This means that a magnitude of the second impedance 702-2 is significantly less than a magnitude of the first impedance 702-1 and is approximately equal to zero. Because the magnitude of the second impedance 702-2 is significantly less than the magnitude of the first impedance 702-1, the second voltage drop 704-2 is also significantly less than the first voltage drop 704-1. In this way, the architecture 600-1 enables different impedances to be presented between the nodes 302 and 304 during transmission and reception such that a voltage drop across the nodes 302 and 304 is less during reception compared to transmission. In this way, the architecture 600-1 enhances sensitivity of the ultrasound system 102 compared to other ultrasound systems that do not include the bypass circuit 602 and enable operation-specific impedance matching 232.

For implementations in which the impedance matching circuit 210 includes multiple series components, some designs can couple the bypass circuit 602 in a manner that bypasses one of the multiple series components that has a largest impedance magnitude of the multiple series components. In the case of FIG. 7-3, the series component 228-1 can have a larger impedance magnitude compared to the series component 228-2. As such, the bypass circuit 602 is coupled in parallel with the series component 228-1 instead of the series component 228-2. Other designs can couple the bypass circuit 602 in a manner that bypasses a set of the multiple series components having a largest combined impedance magnitude compared to a combined impedance magnitude of the remaining series components. These designs can provide a larger amount of sensitivity improvement compared to designs that bypass one or more series components associated with a smaller impedance magnitude.

The bypass circuit 602 can be coupled to the nodes 302 and 304, as shown in FIG. 7-2, or coupled between other nodes associated with the impedance matching circuit 210 for implementations in which the impedance matching circuit 210 includes multiple series components 228, as shown in FIG. 7-3. Consider an example in which the impedance matching circuit 210 includes the series components 228-1 to 228-N and the shunt components 230-1 to 230-N of FIG. 3-2. In a first example, the bypass circuit 602 can be coupled to the nodes 302 and 304 such that all of the components within the impedance matching circuit 210 are bypassed during reception. In a second example, the bypass circuit 602 is coupled to the node 302 and a node that is between the series component 228-1 and the series component 228-2 such that the series component 228-1 is bypassed during reception. In a third example case, the bypass circuit 602 is coupled between the node 302 and a node that is between the series component 228-2 and the series component 228-N such that the series components 228-1 and 228-2 and the shunt component 230-1 are bypassed. In general, the coupling of the bypass circuit 602 to nodes associated with the impedance matching circuit 210 can enable a single series component 228, multiple series components 228, a portion of the series components 228, at least one series component 228 and at least one shunt component 230, or all series components 228 and all shunt components 230 to be bypassed during reception.

Although not explicitly shown in FIGS. 7-2 and 7-3, some implementations of the architecture 600-1 can include the other impedance matching circuit 604 coupled between the bypass circuit 602 and the node 304. The other impedance matching circuit 604 can have an impedance that is significantly smaller than the impedance of the impedance matching circuit 210 between the nodes 302 and 304. As the impedances can represent complex impedances, this means that the magnitude of the impedance of the other impedance matching circuit 602 is significantly less than the magnitude of the impedance of the impedance matching circuit 210. In this way, the one or more series components 228 of the impedance matching circuit 210 are still bypassed during reception and the other impedance matching circuit 604 is associated with a smaller voltage drop to enhance the sensitivity of the ultrasound system 102. Example implementations of the bypass circuit 602 are further described with respect to FIGS. 8-1 to 8-3.

Figures 1, 8:
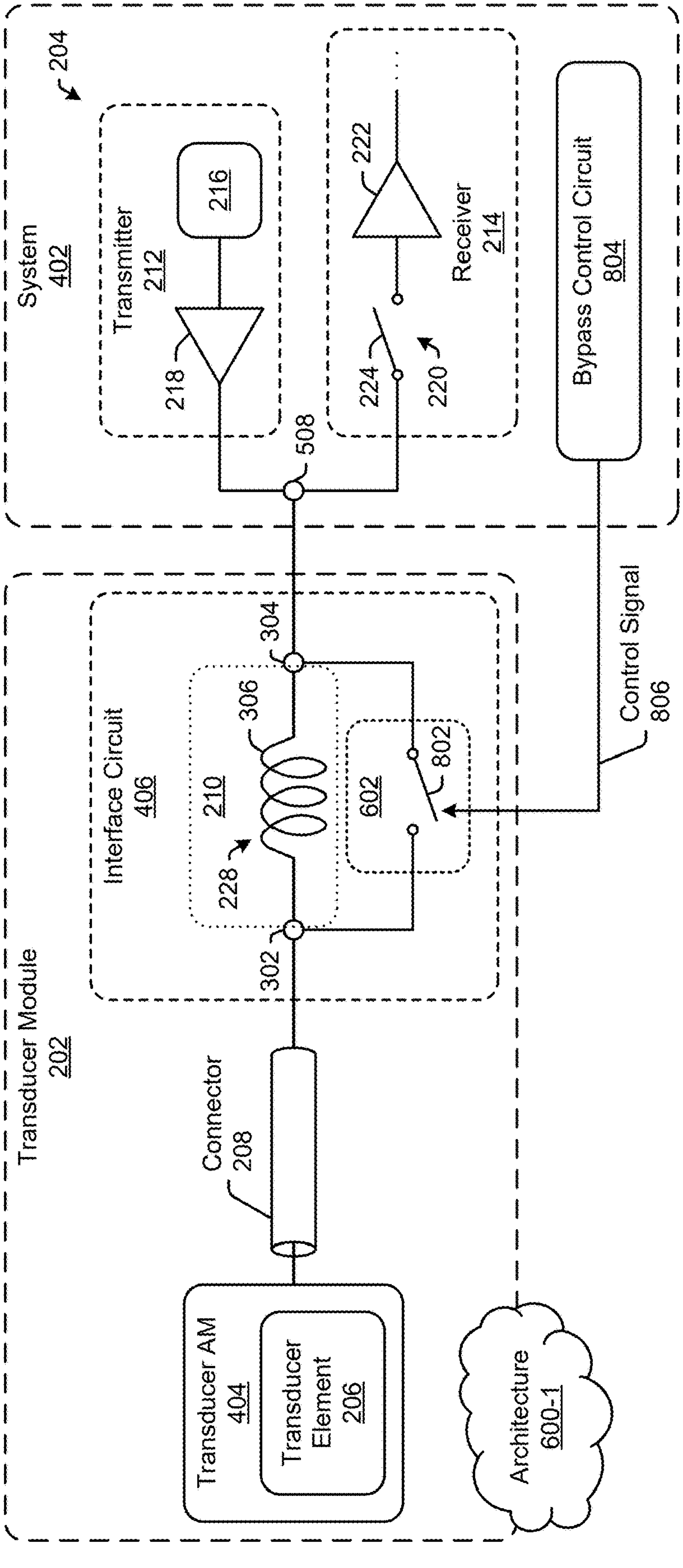
Figures 2, 8:
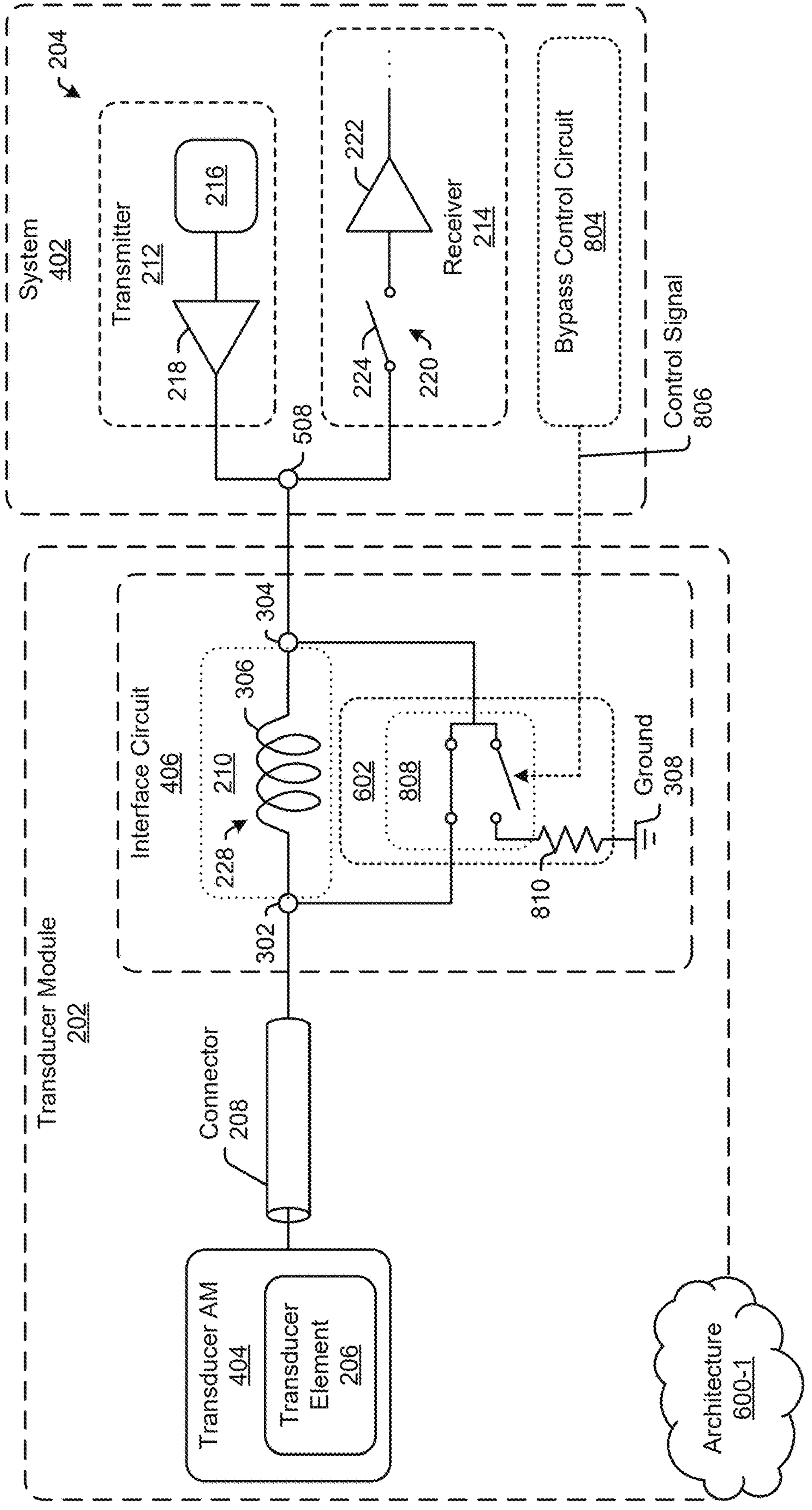
Figures 3, 8:
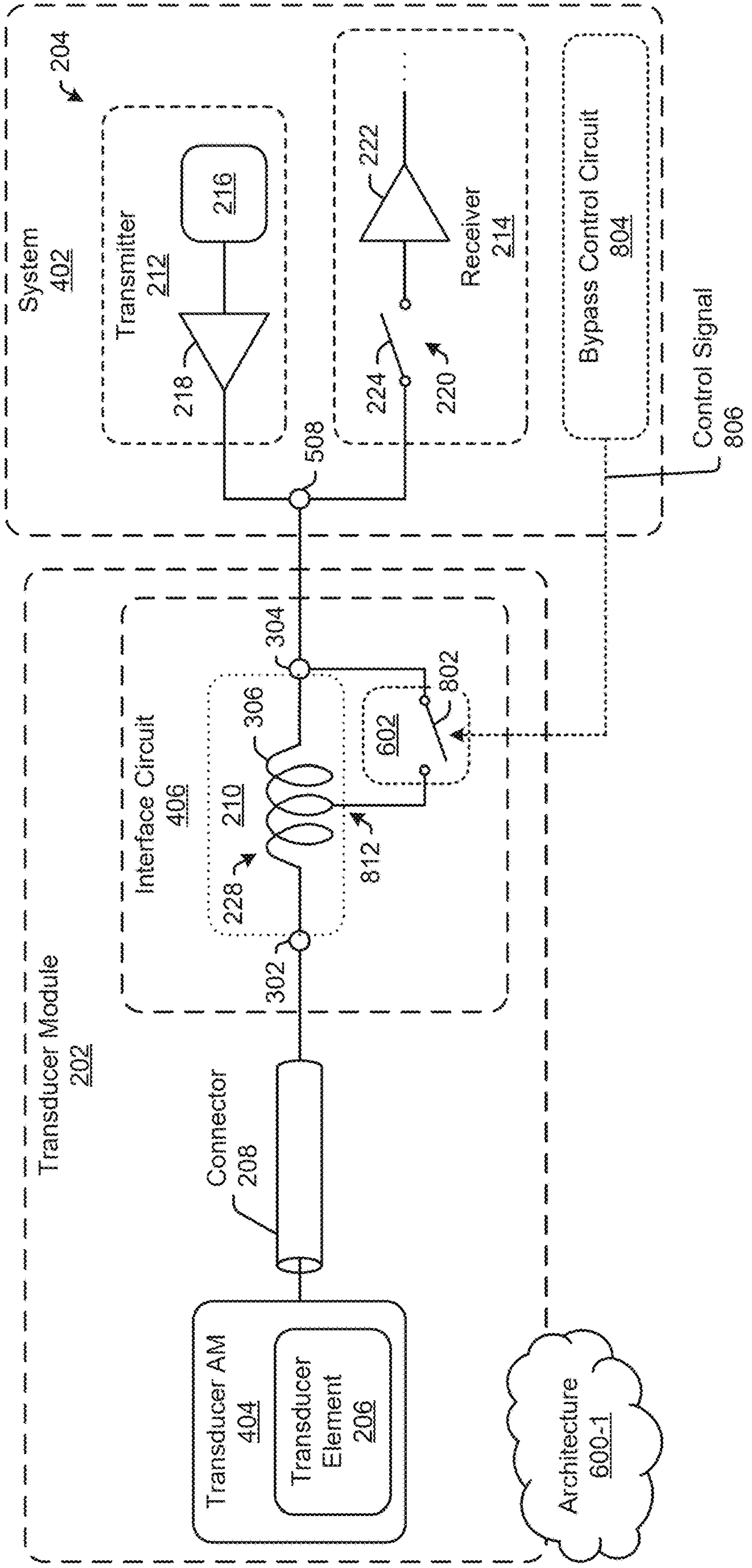

FIG. 8-1 illustrates a first example implementation of the bypass circuit 602. In this example, the bypass circuit 602 is implemented within the interface circuit 406 and includes at least one switch 802. The switch 802 has terminals coupled to the nodes 302 and 304 of the impedance matching circuit 210. The impedance matching circuit 210 includes at least one series component 228, which is coupled between the nodes 302 and 304. In this example, the series component 228 is implemented using the inductor 306, however other implementations are also possible. The node 304 is coupled to the shared node 508.

The system 402 includes the transmitter 212 and the receiver 214, which are coupled to the shared node 508. In this example, the switching circuit 220 of the receiver 214 is shown to be implemented using the transmit/receive switch 224. The system 402 also includes a bypass control circuit 804, which is coupled to the bypass circuit 602. During operation, the bypass control circuit 804 generates a control signal 806, which causes the switch 802 to selectively be in the first state (e.g., the open state) during transmission and be in the second state (e.g., the closed state) during reception.

Implementing the bypass circuit 602 as a switch 802 within the interface circuit 406 can be relatively simple and cost effective. However, additional complexity is involved in modifying an interface between the system 402 and the interface circuit 406 to propagate the control signal 806 from the bypass control circuit 804 to the switch 802. Other implementations of the bypass circuit 602 are also possible to avoid modifying the interface between the interface circuit 406 and the system 402, as further described with respect to FIG. 8-2.

FIG. 8-2 illustrates a second example implementation of the bypass circuit 602. In this example, the bypass circuit 602 is implemented within the interface circuit 406 and includes at least one switching circuit 808 and at least one resistor 810. The switching circuit 808 is coupled between the nodes 302 and 304 and includes a built-in control circuit. The switching circuit 808 also has a particular switching resistance that allows small signals to pass for sensing a voltage drop. With the built-in control circuit, the switching circuit 808 can automatically be in an appropriate state based on the sensed voltage drop to facilitate operation-specific impedance matching 232 for transmission and reception. In particular, the switching circuit 808 can transition from the second state (e.g., the closed state) to the first state (e.g., the open state) based on the sensed voltage drop exceeding a threshold, which can be in the millivolt range. Also, the switching circuit 808 can transition from the first state to the second state based on the sensed voltage drop being less than the threshold. In some cases, the switching circuit 808 can be implemented using a transmit/receive switch, e.g., the transmit/receive switch 224 in FIG. 2. The resistor 810 is coupled between the node 302 and the ground 308. In an example implementation, a resistance of the resistor 810 can be greater than 300 ohms.

The bypass circuit 602 of FIG. 8-2 can be more expensive compared to the bypass circuit 602 of FIG. 8-1. With the switching circuit 808, however, the interface between the interface circuit 406 and the system 402 can remain unchanged.

FIG. 8-3 illustrates a third example implementation in which the interface circuit 406 includes the inductor 306 with a tap 812. In this example, the bypass circuit 602 is coupled between the tap 812 and the node 304. The bypass circuit 602 can be implemented using the switch 802 of FIG. 8-1 or the switching circuit 808 and the resistor 810 of FIG. 8-2. Although the inductor 306 can be considered a single series component 228 in FIG. 8-3, the tap 812 effectively separates the inductor 306 into two portions. In the context of operation-specific impedance matching 232, these portions are similar to the two series components 228-1 and 228-2 described with respect to FIG. 7-3.

During transmission, for instance, the state of the bypass circuit 602 causes the impedance matching circuit 210 to present an entire impedance of the inductor 306 between the nodes 302 and 304. As such, a signal associated with transmission passes through both portions of the inductor 306 from node 304 to node 302. During reception, however, the state of the bypass circuit 602 and the tap causes the impedance matching circuit 210 to present a different impedance between the nodes 302 and 304. This impedance is associated with a second portion of the inductor 306 that is between the node 302 and the tap 812. The bypass circuit 602 causes a signal associated with reception to pass through the second portion of the inductor 306 that is between the node 302 and the tap 812 and pass through the bypass circuit 602 between the tap 812 and the node 304. As such, a first portion of the inductor 306 that is between the tap 812 and the node 304 is bypassed. The impedance presented during reception is smaller in magnitude compared to the impedance presented during transmission, which enhances sensitivity of the ultrasound system 102.

The first architecture 600-1 described above with respect to FIGS. 7-1 to 8-3 includes the impedance matching circuit 210 coupled between the transducer element 206 and the shared node 508. As such, the impedance matching circuit 210 is coupled between two portions of the shared transceiver path 506. More specifically, the nodes 302 and 304 of the impedance matching circuit 210 are disposed within the shared transceiver path 506. Alternatively, in the second architecture 600-2, the impedance matching circuit 210 is coupled to the transducer element 206 via the shared node 508. More specifically, the impedance matching circuit 210 is disposed within the transmit path 502 such that components of the impedance matching circuit 210 are not disposed within the receive path 504, as further described with respect to FIGS. 9-1 and 9-2.

Second Architecture for Enhancing Sensitivity

Figures 1, 9:
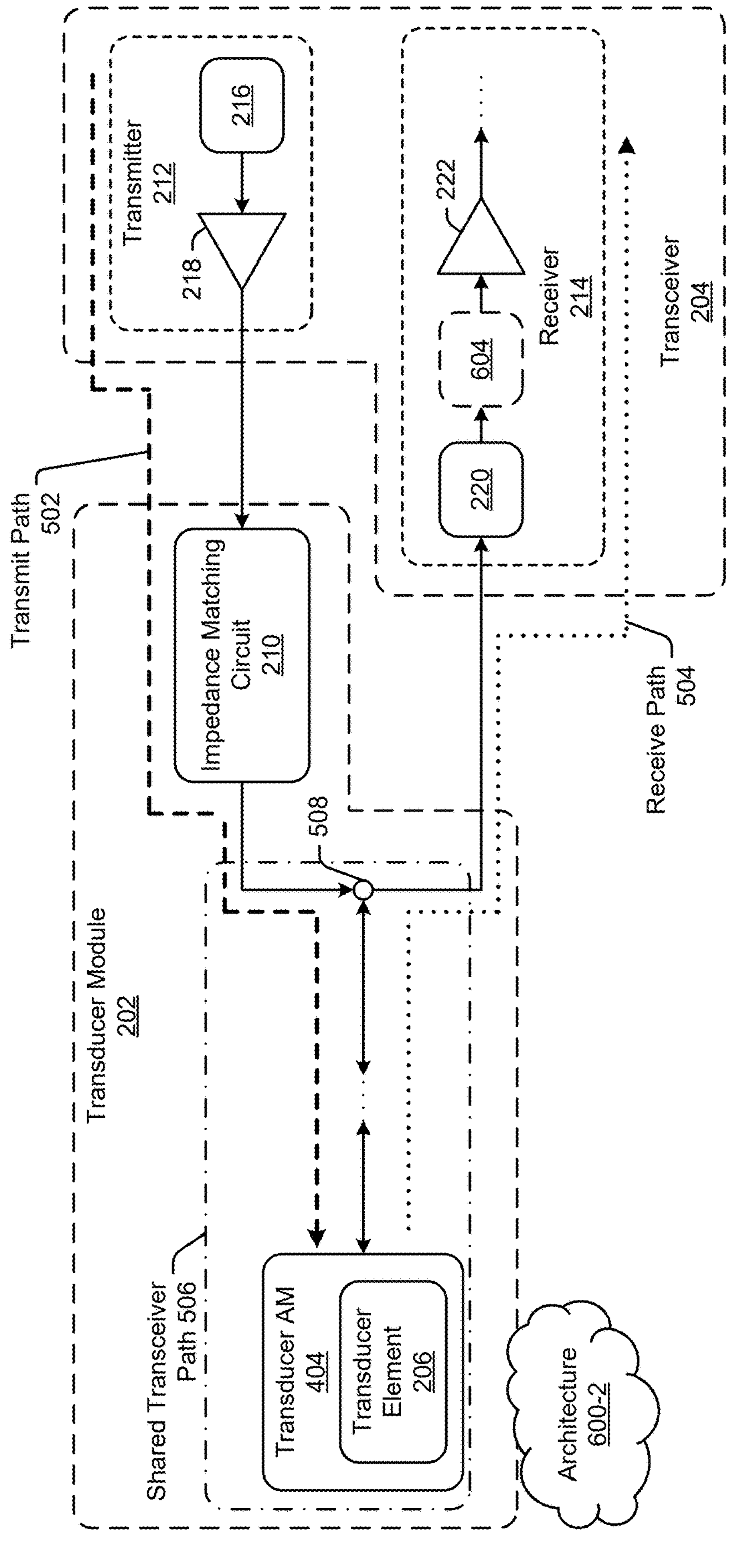
Figures 2, 9:
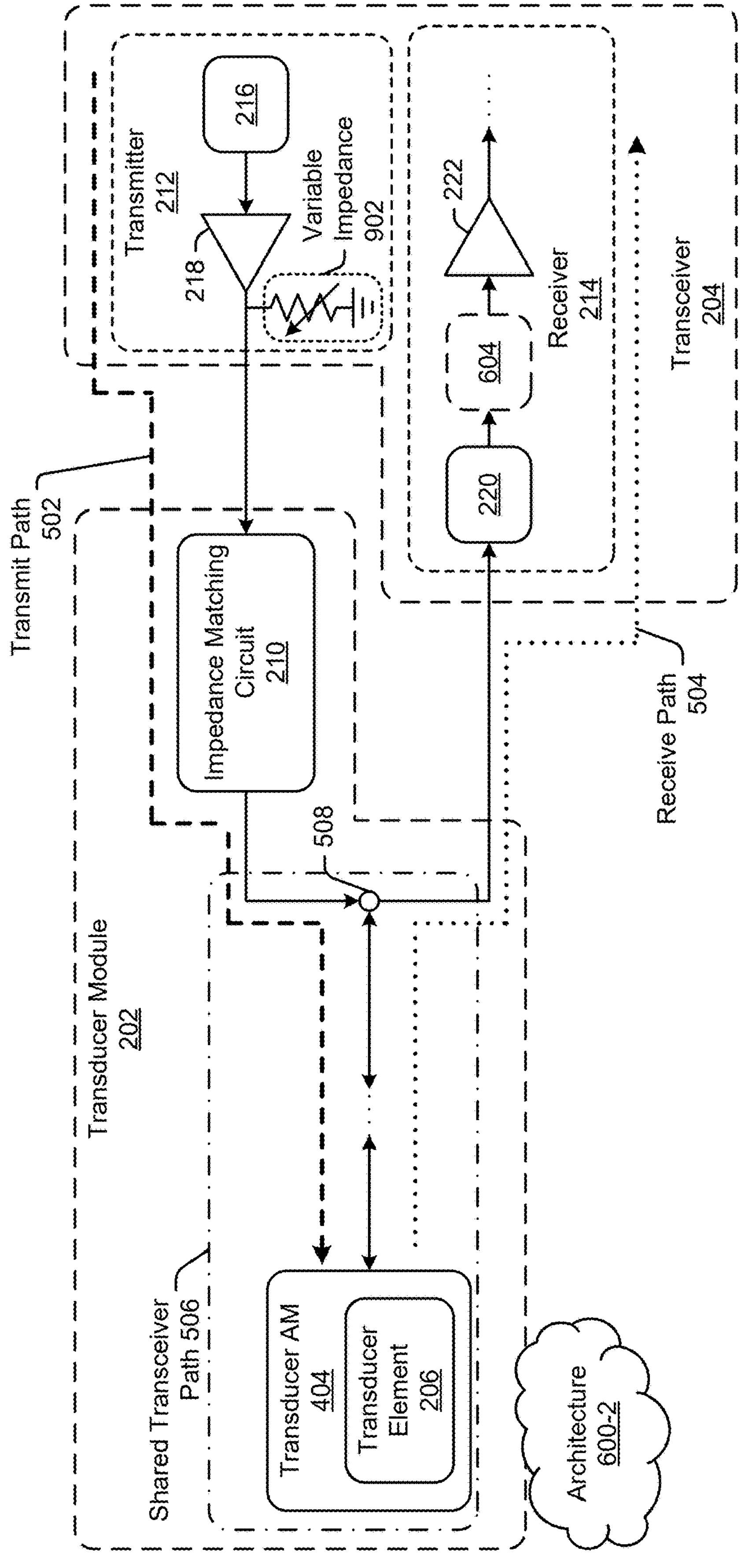

FIG. 9-1 illustrates an example transducer module 202 having the second architecture 600-2 and coupled to a first example transceiver 204. In the depicted configuration, the transducer module 202 includes the transducer array module 404, the shared node 508, and the impedance matching circuit 210. At least the transducer element 206 and the shared node 508 are disposed within the shared transceiver path 506. The transmitter 212 and the receiver 214 are coupled to the shared node 508.

In accordance with the second architecture 600-2, the impedance matching circuit 210 is coupled to the transducer element 206 via the shared node 508. The impedance matching circuit 210 is also coupled between the shared node 508 and the transmitter 212. As such, the impedance matching circuit 210 is disposed within the transmit path 502 and is not disposed within the receive path 504. This means that signals that propagate through the transmit path 502 propagate through the impedance matching circuit 210. However, signals that propagate through the receive path 504 do not propagate through the impedance matching circuit 210. In this way, the impedance matching circuit 210 does not negatively impact the receive sensitivity of the ultrasound system 102 when in receive mode.

Although not explicitly shown in FIG. 9-1, the transducer module 202 also includes the connector 208. The connector

208 may be disposed within the shared transceiver path 506 in some implementations, as shown in FIG. 10-1. In other implementations, the connector 208 may be disposed within the receive path 504, as shown in FIGS. 10-2 and 10-3.

In some implementations, another impedance matching circuit 604 is disposed within the receive path 504 and can be implemented within the receiver 214. The other impedance matching circuit 604 can be implemented with similar components as described with respect to the impedance matching circuit 210 in FIGS. 2 to 3-2. However, an impedance of the other impedance matching circuit 604 has a smaller magnitude compared to the impedance matching circuit 210 to enhance sensitivity of the ultrasound system 102. In this manner, the impedance matching circuit 210 can be designed to enable sufficient power transfer for transmission while the impedance matching circuit 604 can be designed to enable sufficient power transfer for reception without significantly degrading sensitivity of the ultrasound system 102. In some implementations, the transmitter 212 has a variable input impedance, as further described with respect to FIG. 9-2.

FIG. 9-2 illustrates an example transducer module 202 having the second architecture 600-2 and coupled to a second example transceiver 204. The transducer module 202 of FIG. 9-2 is similar to the transducer module 202 of FIG. 9-1. The transceiver 204 of FIG. 9-2, however, differs from the transceiver 204 of FIG. 9-1 in that the transmitter 212 of the transceiver 204 of FIG. 9-2 has a variable impedance 902 at an output of the amplifier 218. In this example, the variable impedance 902 is represented by a variable resistor that is coupled to a ground 308.

In general, the impedance 902 of the transmitter 212 can vary based on different operations. To compensate for the variation in the impedance 902 of the transmitter 212, an impedance of the impedance matching circuit 210 can be adjusted to reduce mismatch loss between the transducer module 202 and the transmitter 212. As the impedance matching circuit 210 is disposed within the transmit path 502 and not the receive path 504, adjustments to the impedance of the impedance matching circuit 210 do not substantially degrade sensitivity of the ultrasound system 102.

In some implementations, the impedance matching circuit 210 is implemented within (or coupled to components of) the interface circuit 406, as described with respect to FIG. 10-1. In other implementations, the impedance matching circuit 210 is implemented within (or coupled to components of) the transducer array module 404, as further described with respect to FIGS. 10-2 and 10-3.

FIG. 10-1 illustrates a first example implementation of the transducer module 202 having the second architecture 600-2. In the depicted configuration, the transducer module 202 includes the transducer array module 404, the connector 208, and the interface circuit 406. The impedance matching circuit 210, the switching circuit 220, and the shared node 508 are implemented within the interface circuit 406. In accordance with the second architecture 600-2, the shared node 508 is between the transducer element 206 and the impedance matching circuit 210, and the impedance matching circuit 210 is disposed within the transmit path 502.

FIG. 10-2 illustrates a second example implementation of the transducer module 202 having the second architecture 600-2. In the depicted configuration, the transducer module 202 includes the transducer array module 404 and the connector 208. In this implementation, the transducer module 202 may not include the interface circuit 406.

Similar to the transducer module 202 of FIG. 10-1, the transducer module 202 of FIG. 10-2 includes the shared node 508 between the transducer element 206 and the impedance matching circuit 210. The transducer module 202 of FIG. 10-2 also includes the impedance matching circuit 210 disposed within the transmit path 502.

In contrast to the transducer module 202 of FIG. 10-1, the transducer module 202 of FIG. 10-2 implements the impedance matching circuit 210 and the shared node 508 within the transducer array module 404 (e.g., within a scanhead or hand-held portion of the scanner 104) instead of within the interface circuit 406 as shown in FIG. 10-1. Also, the transducer module 202 of FIG. 10-2 includes at least some components of the transmitter 212 and the receiver 214, which are also implemented within the transducer array module 404. Although not explicitly shown, the connector 208 can couple the low-noise amplifier 222 of the receiver 214 to other components of the receiver 214 or to other components of the ultrasound system 102 (e.g., the processor 106 and/or the display device 108).

In this example implementation, the system 402 (not shown) generates a control signal 1002. The connector 208 passes the control signal 1002 from the system 402 to the transmitter 212. The control signal 1002 enables the system 402 to control the timing of operations performed by the transmitter 212.

FIG. 10-3 illustrates a third example implementation of the transducer module 202 having the second architecture 600-2. In the depicted configuration, the transducer module 202 includes the transducer array module 404 and the connector 208. The transducer array module 404 includes two transmitters 212-1 and 212-2, which are coupled to the transducer element 206 via the shared node 508. In this example, the second transmitter 212-2 represents additional components that may or may not be utilized during transmission. The transducer array module 404 also includes at least a portion of the receiver 214, which is coupled to the transducer element 206 via the shared node 508. Although not explicitly shown, other portions of the receiver 214 can be implemented within the system 402. In accordance with the second architecture 600-2, the impedance matching circuit 210 is coupled to the transducer element 206 via the shared node 508. The impedance matching circuit 210 is also coupled between the shared node 508 and the first transmitter 212-1.

The transducer array module 404 can optionally include the other impedance matching circuit 604, which is coupled between the switching circuit 220 and the low-noise amplifier 222. The switching circuit 220 includes two transmit/receive switches 224-1 and 224-2. The first transmit/receive switch 224-1 has a first terminal coupled to the impedance matching circuit 210 and the transmitter 212-1, and has a second terminal coupled to another component of the receiver 214 (e.g., the other impedance matching circuit 604 or the low-noise amplifier 222). The second transmit/receive switch 224-2 has a first terminal coupled to the shared node 508 and a second terminal coupled to another component of the receiver 214 (e.g., the other impedance matching circuit 604 or the low-noise amplifier 222).

During transmission, the transmitter 212-1 generates a version of the ultrasound transmit signal 408. The switching circuit 220 is in a first state that causes the transmit/receive switches 224-1 and 224-2 to be in an open state. The architecture 600-2 of the transducer module 202 causes the version of the ultrasound transmit signal 408 to propagate from the transmitter 212-1 to the transducer element 206 through the impedance matching circuit 210 and the shared node 508. The transducer element 206 transmits the ultrasound transmit signal 408.

During reception, the transducer element 206 receives the ultrasound receive signal 410. The switching circuit 220 is in a second state that causes the first transmit/receive switch 224-1 to be in the open state and the second transmit/receive switch 224-2 to be in the closed state. The architecture 600-2 of the transducer module 202 causes a version of the ultrasound receive signal 410 to propagate from the transducer element 206 to the receiver 214 through the shared node 508. The version of the ultrasound receive signal 410 passes through the second transmit/receive switch 224-2 to the other impedance matching circuit 604 (if implemented) and the low-noise amplifier 222.

The second and third example implementations of the transducer module 202 shown in FIGS. 10-2 and 10-3 can reduce requirements associated with the connector 208 and in some cases obviate the use of the interface circuit 406. In this case, an interface between the transducer array module 404 and the system 402 can be simplified compared to the first example implementation shown in FIG. 10-1.

Although the impedance matching circuit 210 can be described as being implemented on-chip in FIGS. 7-1 to 10-3, other implementations are also possible in which the impedance matching circuit 210 (or at least one component of the impedance matching circuit 210) is implemented off-chip. With the architectures 600-1 and 600-2, the ultrasound system 102 can be designed to have various frequency responses that enhance sensitivity, as further described with respect to FIGS. 11-1 to 11-3.

FIGS. 11-1, 11-2, and 11-3 illustrate example frequency responses of different ultrasound systems. Graphs 1100-1, 1100-2, and 1100-3 illustrate three frequency responses 1102, 1104, and 1106, which are associated with different ultrasound systems. A first frequency response 1102 is associated with a first ultrasound system that does not employ the techniques for enhancing sensitivity using operation-specific impedance matching 232. In other words, the first ultrasound system has an impedance matching circuit that is disposed in the shared transceiver path 506 such that the impedance matching circuit 210 is utilized for both transmission and reception.

A second frequency response 1104 is associated with a second ultrasound system 102 that utilizes the techniques for enhancing sensitivity using operation-specific impedance matching 232. The second ultrasound system 102 can have the first architecture 600-1 or the second architecture 600-2. In comparison to the first frequency response 1102, the second frequency response 1104 has a significantly higher amplitude. In some cases, the amplitude of the second frequency response 1104 is several decibels higher than the amplitude of the first frequency response 1102 (e.g., at least 2, 3, 4, 6, or 10 dB higher). This means that the second ultrasound system 102 has enhanced sensitivity relative to the first ultrasound system.

A third frequency response 1106 is associated with a third ultrasound system 102 that also utilizes the techniques for enhancing sensitivity using operation-specific impedance matching 232. The third ultrasound system 102 can have the first architecture 600-1 or the second architecture 600-2. The third ultrasound system 102 also includes the other impedance matching circuit 604, which is disposed within the receive path 504.

Figures 1, 11:
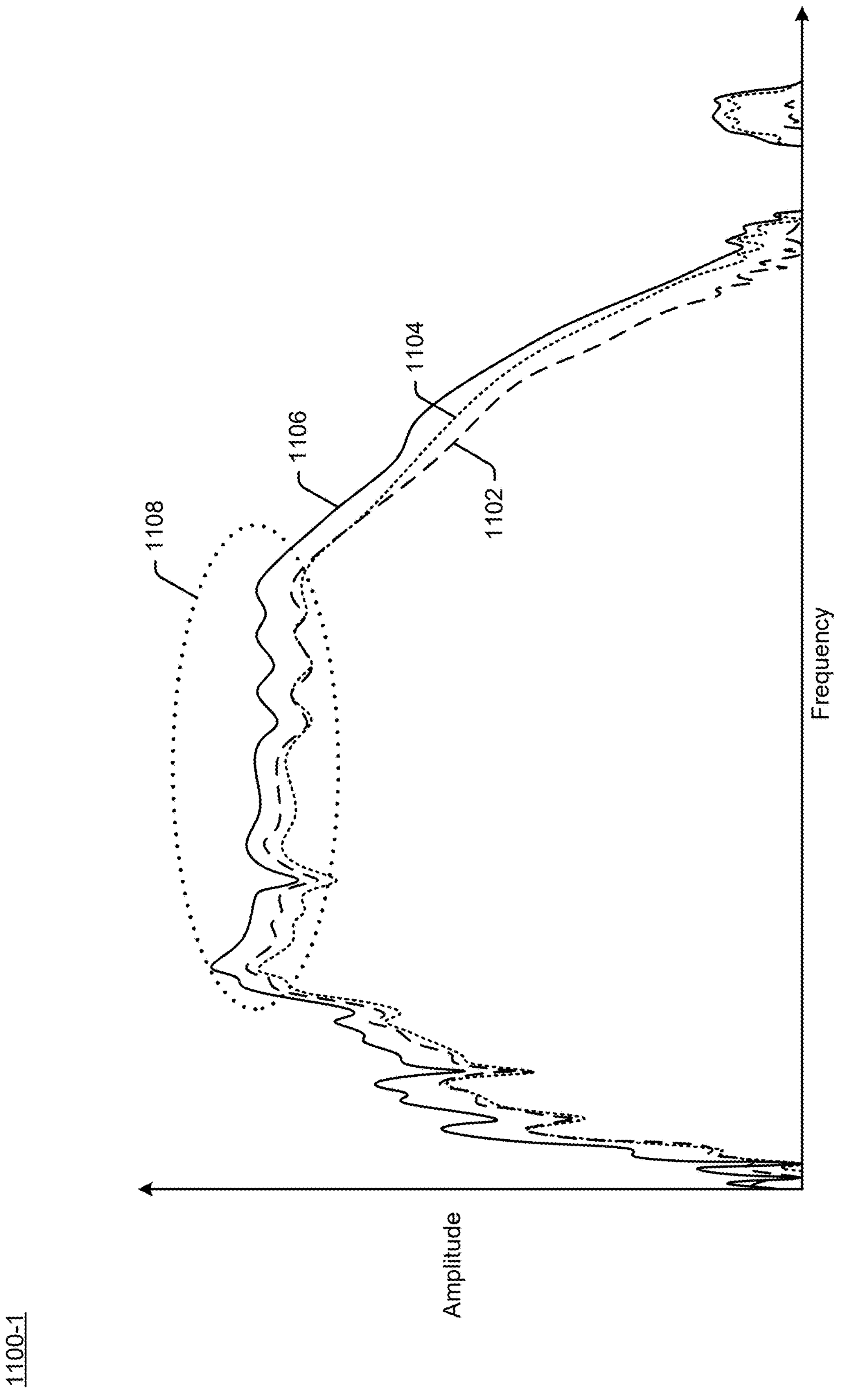
Figures 2, 11:
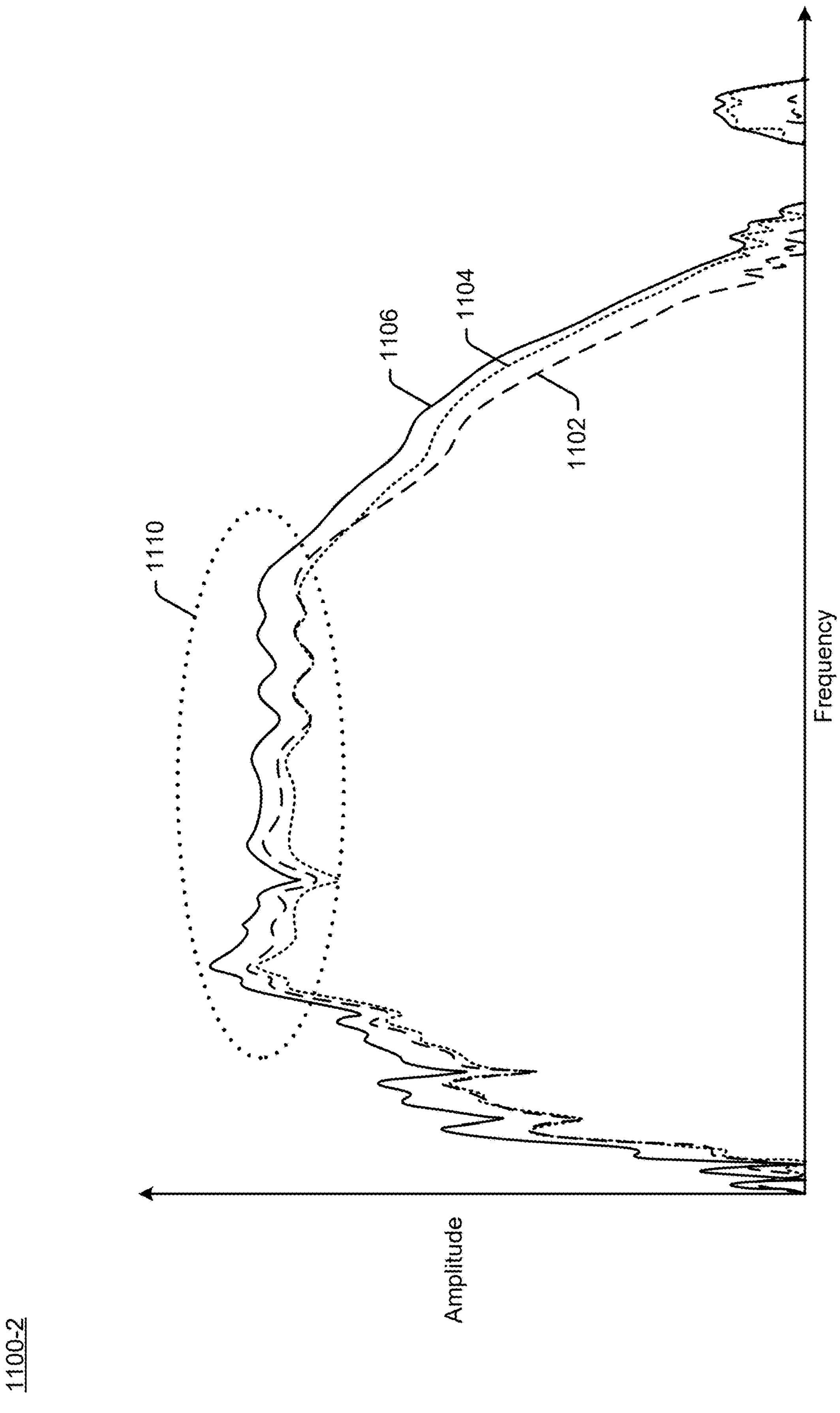
Figures 3, 11:
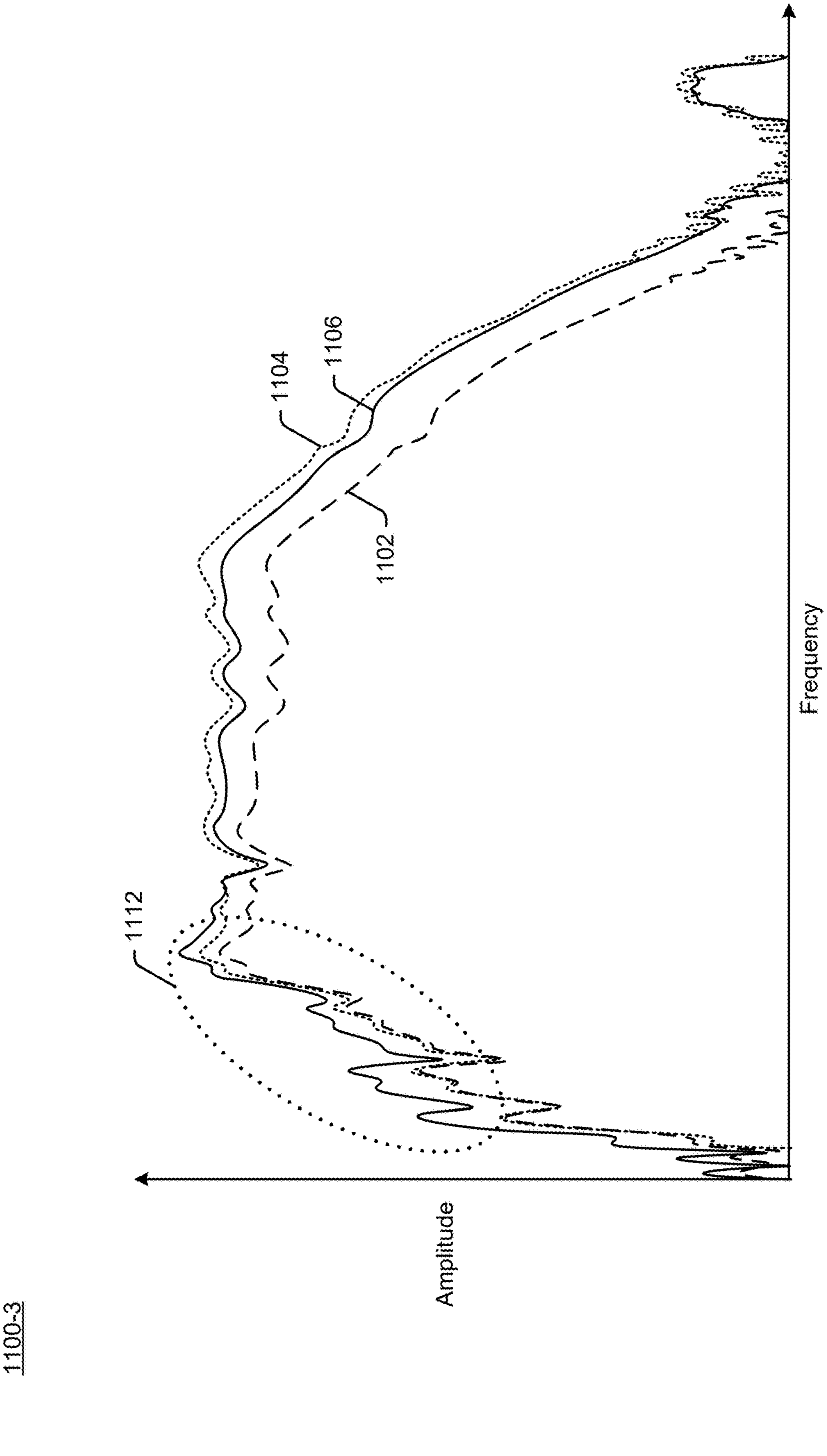

FIG. 11-1 illustrates example second and third frequency responses 1104 and 1106 associated with the first architecture 600-1 shown in FIGS. 8-1 and 8-2, and the second architecture 600-2 shown in FIG. 9-1. The implementations shown in FIGS. 8-1, 8-2, and 9-1 can include the complete bypassing of an inductor 306 within the interface circuit 406 during reception. In this example, the third frequency response 1106 is tuned to improve sensitivity across a middle portion of the frequency range, as shown generally at 1108.

FIG. 11-2 illustrates example second and third frequency responses 1104 and 1106 associated with the first architecture 600-1 shown in FIG. 8-3. The implementation shown in FIG. 8-3 can cause a portion of the inductor 306 (e.g., half of the inductor 306) to be bypassed during reception. In this example, the third frequency response 1106 is tuned to improve sensitivity across a middle portion of the frequency range, as shown generally at 1110.

FIG. 11-3 illustrates example second and third frequency responses 1104 and 1106 associated with the second architecture 600-2 shown in FIG. 9-2. With the other impedance matching circuit 604, the third frequency response 1106 is tuned to improve sensitivity within the lower portion of the frequency range, as shown generally at 1112. In general, the architectures 600-1 and 600-2 provide additional flexibility for tuning the frequency response of the ultrasound system 102 by enhancing sensitivity at some specific frequency range.

Example Methods

Methods 1200 and 1300 are shown as a set of blocks that specify operations performed but are not necessarily limited to the order or combinations shown for performing the operations by the respective blocks. Further, any of one or more of the operations can be repeated, combined, reorganized, omitted, or linked to provide a wide array of additional and/or alternate methods. In portions of the following discussion, reference may be made to the example ultrasound system 102 of FIG. 1 or to entities or processes as detailed in FIGS. 2 to 10-3, reference to which is made for example only. The techniques are not limited to performance by one entity or multiple entities operating on one device.

Figure 12:
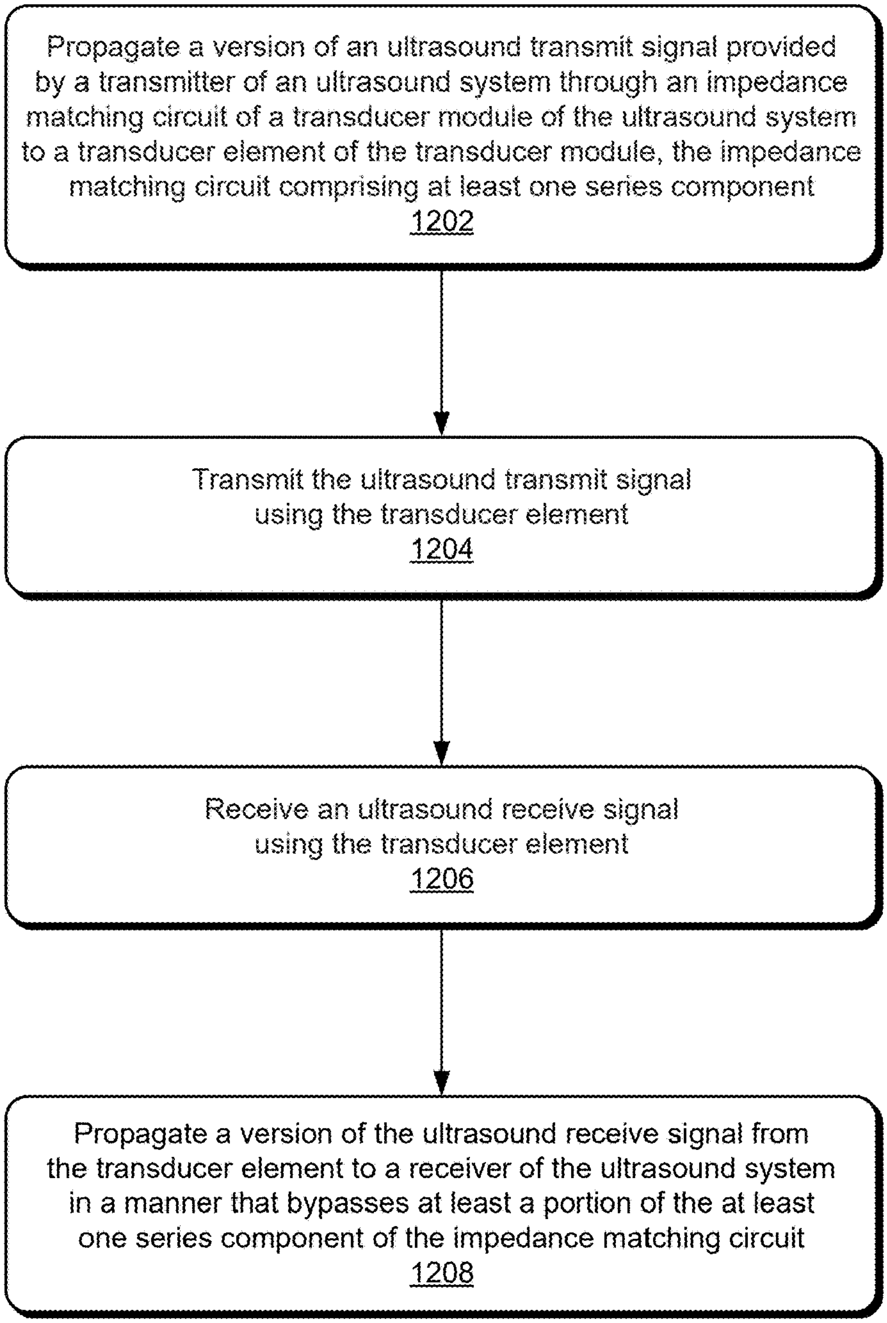
FIG. 12 depicts a first example method for enhancing sensitivity of an ultrasound system.

FIG. 12 depicts a method 1200 for enhancing sensitivity of an ultrasound system using an architecture of a transducer module. The method 1200 is generally performed by the ultrasound system 102 described herein. More specifically, the method 1200 can be performed by the transducer module 202. At 1202, a version of an ultrasound transmit signal provided by a transmitter of an ultrasound system is propagated through an impedance matching circuit of a transducer module of the ultrasound system to a transducer element of the transducer module. The impedance matching circuit comprises at least one series component.

For example, an architecture of the transducer module 202 propagates a version of the ultrasound transmit signal 408, which is provided by the transmitter 212 of the ultrasound system 102, through the impedance matching circuit 210 to the transducer element 206, as shown in FIGS. 4 and 5. The transducer module 202 can have the first architecture 600-1 or the second architecture 600-2, as described with respect to FIG. 6. The version of the ultrasound transmit signal 408 represents a transmit signal that is used to generate the ultrasound transmit signal 408.

The impedance matching circuit 210 includes at least one series component 228. Example implementations of the impedance matching circuit 210 are shown in FIGS. 3-1 and 3-2. In some cases, the series component 228 is an inductor 306. However, the series component 228 can generally include any type of lumped or distributed element.

At 1204, the ultrasound transmit signal is transmitted using the transducer element. For example, the transducer element 206 transmits the ultrasound transmit signal 408.

At 1206, the ultrasound receive signal is received using the transducer element. For example, the transducer element 206 receives the ultrasound receive signal 410. The ultrasound receive signal 410 can represent a version of the ultrasound transmit signal 408 that is reflected by an object associated with the subject 114. The ultrasound receive signal 410 can be received during a time interval that occurs after the ultrasound transmit signal 408 is transmitted.

At 1208, a version of the ultrasound receive signal is propagated from the transducer element to a receiver of the ultrasound system in a manner that bypasses at least a portion of the at least one series component of the impedance matching circuit. For example, the architecture of the transducer module 202 propagates a version of the ultrasound receive signal 410 from the transducer element 206 to the receiver 214 in a manner that bypasses at least a portion of the at least one series component 228 of the impedance matching circuit 210. In this way, the architecture of the transducer module 202 provides operation-specific impedance matching 232, which enhances sensitivity of the ultrasound system 102. The portion of the at least one series component 228 can refer to one of multiple series components 228 within the impedance matching circuit 210, half (or some other fraction) of a single series component 228 (e.g., the inductor 306 of FIG. 8-3), or all of the one or more series components 228 within the impedance matching circuit 210. With enhanced sensitivity, the ultrasound system 102 can utilize higher frequencies and/or broader bandwidths to provide high-resolution images at farther imaging depths without increasing power densities.

Figure 13:
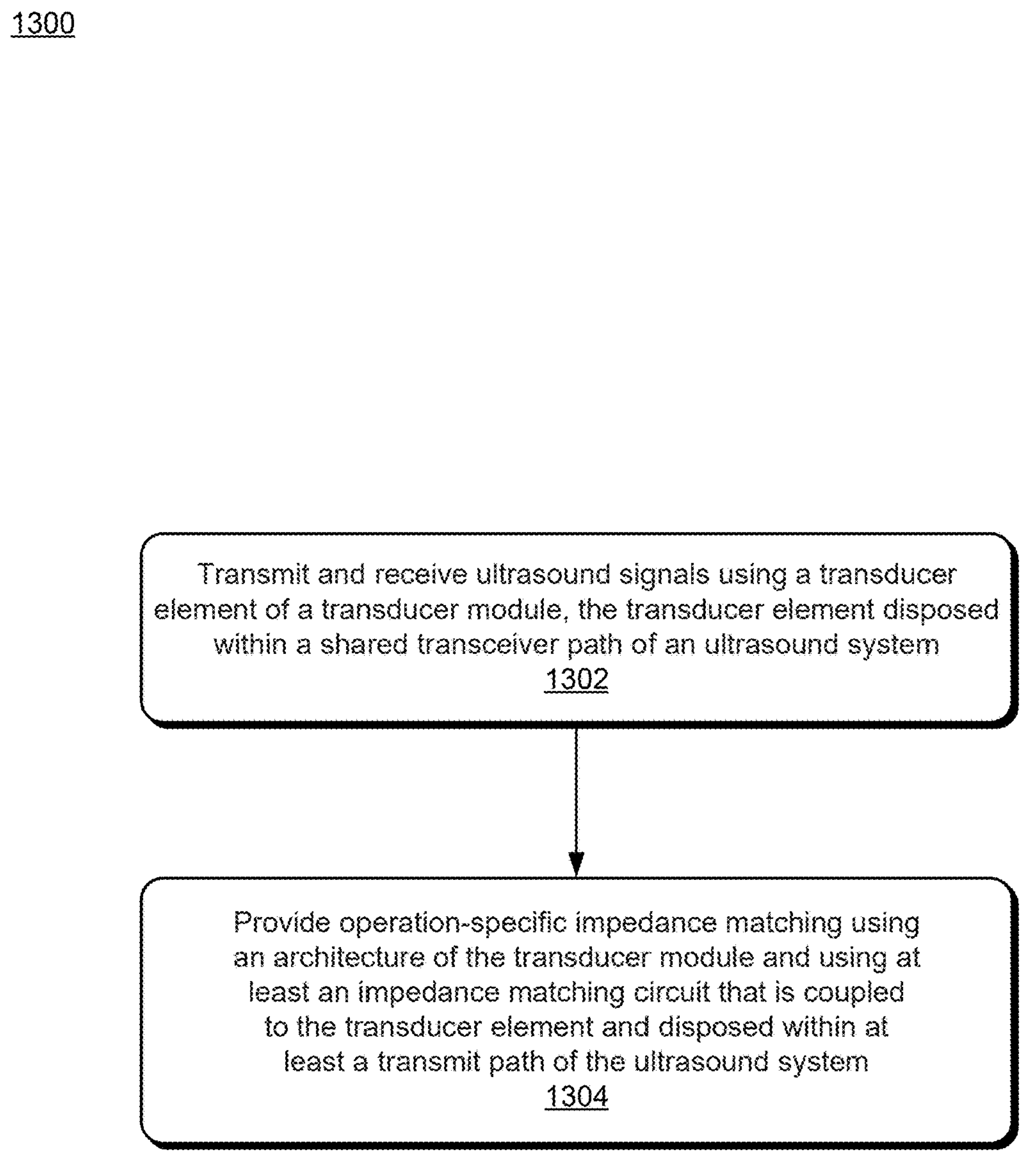
FIG. 13 depicts a second example method for enhancing sensitivity of an ultrasound system.

FIG. 13 depicts another method 1300 for enhancing sensitivity of an ultrasound system. The method 1300 is generally performed by the ultrasound system 102 described herein. More specifically, the method 1300 can be performed by the transducer module 202 described herein. At 1302, ultrasound signals are transmitted and received using a transducer element of a transducer module. The transducer element is disposed within a shared transceiver path of an ultrasound system. For example, the transducer element 206 of the transducer module 202 transmits and receives ultrasound signals, as shown in FIG. 4. The transducer element 206 is disposed within the shared transceiver path 506 of the ultrasound system 102, as shown in FIG. 5.

At 1304, operation-specific impedance matching is provided using an architecture of the transducer module and using at least an impedance matching circuit that is coupled to the transducer and disposed within at least a transmit path of the ultrasound system. For example, the architecture of the transducer module 202 provides impedance matching using at least the impedance matching circuit 210 that is coupled to the transducer element 206 and disposed within at least the transmit path 502 of the ultrasound system 102. The transducer module 202 can have the first architecture 600-1 or the second architecture 600-2 to provide the operation-specific impedance matching 232, as described with respect to FIG. 6.

Operation-specific impedance matching 232 means that different impedances are provided during transmission and reception for impedance matching (e.g., for mitigating mismatch loss). For example, a first impedance is provided between the transmitter 212 and the transducer element 206 for transmission. A second impedance is provided between the transducer element 206 and the receiver 214 for reception. The first impedance is different than the second impedance. In some cases, the first impedance is significantly larger in magnitude compared to the second impedance. The second impedance can also be approximately equal to zero in some architectures. With operation-specific impedance matching 232, the ultrasound system 102 can have enhanced sensitivity. This enables the ultrasound system 102 to utilize higher frequencies and/or broader bandwidths to provide high-resolution images at farther imaging depths without increasing power densities.

CONCLUSION

Embodiments of enhancing sensitivity in an ultrasound system as described herein are advantageous, as they can enable the ultrasound system to utilize higher frequencies and/or broader bandwidths to provide high-resolution images at farther imaging depths without increasing power densities. Although the techniques described herein are directed to ultrasound systems used in medical facilities, the techniques can also be applied to other types of ultrasound systems.

Some examples are described below.

Example 1: An apparatus comprising:

a transducer module of an ultrasound system, the transducer module comprising:
- a transducer element configured to:
  - be coupled to a transmitter and a receiver of the ultrasound system;
  - transmit an ultrasound transmit signal during a first time interval; and
  - receive an ultrasound receive signal during a second time interval that differs from the first time interval; and
- an impedance matching circuit coupled to the transducer element, the transducer module having an architecture configured to:
- propagate a version of the ultrasound transmit signal provided by the transmitter in a manner that passes through the impedance matching circuit to the transducer element during the first time interval; and
- propagate a version of the ultrasound receive signal from the transducer element to the receiver in a manner that bypasses at least a portion of the impedance matching circuit during the second time interval.

Example 2: The apparatus of example 1, wherein:

the impedance matching circuit comprises at least one series component; and the architecture of the transducer module is configured to:
- cause the ultrasound transmit signal to pass through the at least one series component during the first time interval; and
- cause the ultrasound receive signal to bypass at least the portion of the at least one series component during the second time interval.

Example 3: The apparatus of example 2, wherein the at least one series component comprises an inductor.

Example 4: The apparatus of example 3, wherein the architecture of the transducer module is configured to:

cause the ultrasound transmit signal to pass through the inductor during the first time interval;

cause the ultrasound receive signal to pass through a first portion of the inductor during the second time interval; and cause the ultrasound receive signal to bypass a second portion of the inductor during the second time interval.

Example 5: The apparatus of example 3, wherein the architecture of the transducer module is configured to:

cause the ultrasound transmit signal to pass through the inductor during the first time interval; and cause the ultrasound receive signal to bypass the inductor during the second time interval.

Example 6: The apparatus of example 2 or 3, wherein:

the at least one series component comprises multiple series components; and the architecture of the transducer module is configured to cause the ultrasound receive signal to bypass a first set of the multiple series components and pass through a second set of the multiple series components.

Example 7: The apparatus of any one of examples 2 to 6, wherein:

the transducer module comprises a bypass circuit coupled in parallel with the at least one series component; and the bypass circuit is configured to selectively:

be in a first state to cause current to flow through the at least on series component during the first time interval; and be in a second state to cause the current to flow through the bypass circuit during the second time interval.

Example 8: The apparatus of example 7, wherein:

the transducer module is configured to be coupled to a system; and the bypass circuit is configured to:

receive a control signal from the system; and selectively be in the first state during the first time interval and be in the second state during the second time interval based on the control signal.

Example 9: The apparatus of example 7 or 8, wherein the transducer module comprises:

a first integrated circuit comprising the transducer element;

a second integrated circuit comprising the impedance matching circuit and the bypass circuit; and a connector configured to couple the first integrated circuit to the second integrated circuit.

Example 10: The apparatus of any one of examples 1 to 3, wherein the architecture of the transducer module is configured to propagate the version of the ultrasound receive signal from the transducer element to the receiver in a manner that bypasses an entirety of the impedance matching circuit.

Example 11: The apparatus of example 10, wherein the transducer module comprises a switching circuit, the switching circuit comprising:

a first terminal coupled to a node that is between the impedance matching circuit and the transducer element; and a second terminal configured to be coupled to an amplifier of the receiver.

Example 12: The apparatus of example 11, wherein the switching circuit is configured to selectively:

be in a first state to isolate the amplifier from the node during the first time interval; and be in a second state to connect the amplifier to the node during the second time interval.

Example 13: The apparatus of example 11 or 12, wherein the transducer module comprises:

a first integrated circuit comprising the transducer element;

a second integrated circuit comprising the impedance matching circuit and the switching circuit; and a connector configured to couple the first integrated circuit to the second integrated circuit.

Example 14: The apparatus of example 11 or 12, wherein the transducer module comprises an integrated circuit comprising the transducer element, the impedance matching circuit, and the switching circuit.

Example 15: The apparatus of any one of examples 11 to 14, wherein the transducer module comprises a second impedance matching circuit that is coupled between the second terminal of the switching circuit and the amplifier of the receiver.

Example 16: The apparatus of any one of the previous examples, wherein:

the transducer module comprises a transducer array module configured to be connected to at least one connector of the ultrasound system; and the transducer array module comprises the transducer element, the impedance matching circuit, at least a portion of the transmitter, and at least a portion of the receiver.

Example 17: The apparatus of any one of the previous examples, wherein the transducer module comprises:

a transducer array module comprising the transducer element;

an interface circuit comprising the impedance matching circuit; and at least one connector configured to couple the transducer array module to the interface circuit.

Example 18: A method for enhancing sensitivity of an ultrasound system, the method comprising:

propagating a version of an ultrasound transmit signal provided by a transmitter of the ultrasound system through an impedance matching circuit of a transducer module of the ultrasound system to a transducer element of the transducer module, the impedance matching circuit comprising at least one series component;

transmitting the ultrasound transmit signal using the transducer element;

receiving an ultrasound receive signal using the transducer element; and propagating a version of the ultrasound receive signal from the transducer element to a receiver of the ultrasound system in a manner that bypasses at least a portion of the at least one series component of the impedance matching circuit.

Example 19: The method of example 18, wherein:

the propagating of the version of the ultrasound transmit signal comprises providing a first impedance between two nodes associated with the at least one series component; and the propagating of the version of the ultrasound receive signal comprises providing a second impedance between the two nodes associated with the at least one series component, the second impedance being less than the first impedance.

Example 20: The method of example 18 or 19, wherein:

the at least one series component of the impedance matching circuit comprises an inductor;

the propagating of the version of the ultrasound transmit signal comprises propagating the version of the ultrasound transmit signal through the inductor; and the propagating the version of the ultrasound receive signal comprises:

propagating the version of the ultrasound receive signal through a first portion of the inductor; and causing the ultrasound receive signal to bypass a second portion of the inductor.

Example 21: The method of example 18 or 19, wherein:

the at least one series component of the impedance matching circuit comprises a first series component and a second series component; and the propagating of the version of the ultrasound receive signal comprises propagating the version of the ultrasound receive signal from the transducer element to the receiver in a manner that bypasses the first series component and passes through the second series component.

Example 22: The method of example 18, wherein the propagating of the version of the ultrasound receive signal comprises propagating the version of the ultrasound receive signal from the transducer element to the receiver through a node that is between the transducer element and the impedance matching circuit to bypass an entirety of the impedance matching circuit.

Example 23: The method of example 22, wherein the propagating of the version of the ultrasound receive signal through the node comprises propagating the version of the ultrasound receive signal through a second impedance matching circuit that is between the node and a low-noise amplifier of the receiver.

Example 24: A transducer module of an ultrasound system, the transducer module comprising:
- a transducer element disposed within a shared transceiver path of the ultrasound system and configured to transmit and receive ultrasound signals;
- an impedance matching circuit coupled to the transducer element and disposed within at least a transmit path of the ultrasound system; and
- an architecture that causes operation-specific impedance matching to be provided using at least the impedance matching circuit.

Example 25: The transducer module of example 24, wherein:
- a portion of the impedance matching circuit is disposed within a receive path of the ultrasound system; and
- the architecture of the transducer module causes the operation-specific impedance matching to be provided using the impedance matching circuit for transmission and using the portion of the impedance matching circuit for reception.

Example 26: The transducer module of example 24, wherein:
- the impedance matching circuit comprises at least one series component; and
- the transducer module comprises a bypass circuit configured to bypass at least a portion of the at least one series component of the impedance matching circuit for reception.

Example 27: The transducer module of example 24, wherein:
- the transducer module comprises a switching circuit, the switching circuit comprising:
  - a first terminal coupled to a node that is between the impedance matching circuit and the transducer element; and
  - a second terminal configured to be coupled to an amplifier of a receiver of the ultrasound system; and
- the switching circuit is configured to selectively:
  - be in a first state to isolate the amplifier from the node for transmission; and
  - be in a second state that connects the amplifier to the node and enables the impedance matching circuit to be bypassed for reception.

Example 28: The transducer module of example 24 or 27, wherein:
- the impedance matching circuit comprises a first impedance matching circuit disposed within the transmit path;
- the transducer module comprises a second impedance matching circuit coupled to the transducer element and disposed within a receive path of the ultrasound system; and
- the architecture of the transducer module causes the operation-specific impedance matching to be provided using the first impedance matching circuit for transmission and the second impedance matching circuit for reception.

Example 29: An apparatus comprising:
- a transducer module of an ultrasound system, the transducer module comprising:
  - a transducer element;
  - an impedance matching circuit configured to be coupled between the transducer element and a node that is disposed within a transmit path and a receive path of the ultrasound system; and
  - a bypass circuit coupled to the node and configured to selectively:
    - be in a first state during transmission to cause current to pass from the node to the transducer element through the impedance matching circuit; and
    - be in a second state during reception to cause the current to pass from the transducer element to the node in a manner that bypasses at least a portion of the impedance matching circuit.

Example 30: The apparatus of example 29, wherein:
- the transducer module comprises:
  - a transducer array module comprising the transducer element;
  - an interface circuit comprising the impedance matching circuit and the bypass circuit; and
  - at least one connector configured to couple the transducer array module to the interface circuit.

Example 31: The apparatus of example 29 or 30, wherein:
- the impedance matching circuit comprises a series component having:
  - a first terminal that is coupled to the transducer element; and
  - a second terminal that is configured to be coupled to the node; and the bypass circuit comprises a switch having:
  - a first terminal that is coupled to the first terminal of the series component; and
  - a second terminal that is coupled to the second terminal of the series component.

Example 32: The apparatus of example 31, wherein the switch is configured to selectively:
- be in an open state during transmission; and
- be in a closed state during reception.

Example 33: The apparatus of example 31 or 32, wherein the bypass circuit comprises:
- a resistor having a first terminal and a second terminal configured to be coupled to a ground; and
- a second switch having:
  - a first terminal coupled to the first terminal of the resistor; and
  - a second terminal coupled to the second terminal of the series component and the second terminal of the switch.

Example 34: The apparatus of example 29 or 30, wherein:
- the impedance matching circuit comprises a series component having:
  - a first terminal that is coupled to the transducer element; and
  - a second terminal that is configured to be coupled to the node; and the bypass circuit comprises a switch having:

a first terminal that is coupled to a tap that is between the first terminal of the series component and the second terminal of the series component; and a second terminal that is coupled to the second terminal of the series component.

Example 35: An apparatus comprising:

a transducer module of an ultrasound system, the transducer module comprising:

a transducer element coupled to a node that is disposed within a transmit path and a receive path of the ultrasound system;

an impedance matching circuit disposed within the transmit path and configured to be coupled between the node and a transmitter of the ultrasound system; and a switching circuit disposed within the receive path and configured to be coupled between the node and a receiver of the ultrasound system.

Example 36: The apparatus of example 35, wherein the switching circuit comprises a switch having:

a first terminal coupled to the node; and a second terminal configured to be coupled to the receiver.

Example 37: The apparatus of example 36, wherein the switch is configured to selectively:

be in an open state during transmission; and be in a closed state during reception.

Example 38: The apparatus of any one of examples 35 to 37, wherein the impedance matching circuit comprises at least one inductor.

Example 39: The apparatus of any one of examples 35 to 38, wherein the transducer module comprises:

a transducer array module comprising the transducer element;

an interface circuit comprising the impedance matching circuit, the switching circuit, and the node; and at least one connector configured to couple the transducer array module to the interface circuit.

Example 40: The apparatus of any one of examples 35 to 38, wherein:

the transducer module comprises a transducer array module; and the transducer array module comprises the transducer element, the impedance matching circuit, the switching circuit, and the node.

Example 41: The apparatus of example 40, wherein the transducer array module comprises:

a first amplifier having an output coupled to the impedance matching circuit, the first amplifier associated with the transmitter; and a second amplifier having an input coupled to the switching circuit, the second amplifier associated with the receiver.

Example 42: The apparatus of example 41, wherein the transducer array module comprises a second impedance matching circuit coupled between the switching circuit and the input of the second amplifier.

Example 43: The apparatus of example 42, wherein a magnitude of an impedance of the second impedance matching circuit is less than a magnitude of an impedance of the impedance matching circuit.

What is claimed is:

1. An apparatus comprising:

a transducer module of an ultrasound system, the transducer module comprising:

a transducer element configured to:

be coupled to a transmitter and a receiver of the ultrasound system;

transmit an ultrasound transmit signal during a first time interval; and receive an ultrasound receive signal during a second time interval that differs from the first time interval; and an impedance matching circuit coupled to the transducer element, the transducer module having an architecture configured to:

propagate a version of the ultrasound transmit signal provided by the transmitter in a manner that passes through first and second portions of the impedance matching circuit to the transducer element during the first time interval; and propagate a version of the ultrasound receive signal from the transducer element to the receiver in a manner that bypasses the first portion of the impedance matching circuit during the second time interval and that passes through the second portion of the impedance matching circuit during the second time interval.

2. The apparatus of claim 1, wherein:

the impedance matching circuit comprises at least one series component; and the architecture of the transducer module is configured to:

cause the ultrasound transmit signal to pass through the first and second portions of the at least one series component during the first time interval;

cause the ultrasound receive signal to bypass the first portion of the at least one series component during the second time interval; and cause the ultrasound receive signal to pass through the second portion of the at least one series component during the second time interval.

3. The apparatus of claim 2, wherein the at least one series component comprises an inductor.

4. The apparatus of claim 3, wherein the architecture of the transducer module is configured to:

cause the ultrasound transmit signal to pass through the first and second portions of the inductor during the first time interval;

cause the ultrasound receive signal to pass through the second portion of the inductor during the second time interval; and cause the ultrasound receive signal to bypass the first portion of the inductor during the second time interval.

5. The apparatus of claim 4, wherein:

the inductor comprises a tap; and the architecture of the transducer module is configured to:

cause the ultrasound receive signal to pass through the second portion of the inductor that is between the transducer element and the tap; and cause the ultrasound receive signal to bypass the first portion of the inductor that is between the tap and the receiver.

6. The apparatus of claim 2, wherein:

the at least one series component comprises multiple series components; and the architecture of the transducer module is configured to cause the ultrasound receive signal to bypass a first set of the multiple series components and pass through a second set of the multiple series components.

7. The apparatus of claim 2, wherein:

the transducer module comprises a bypass circuit coupled in parallel with the first portion of the at least one series component; and the bypass circuit is configured to selectively:

be in a first state to cause current to flow through the first portion of the at least on series component during the first time interval; and be in a second state to cause the current to flow through the bypass circuit during the second time interval.

8. The apparatus of claim 7, wherein:

the transducer module is configured to be coupled to a system; and the bypass circuit is configured to:

receive a control signal from the system; and selectively be in the first state during the first time interval and be in the second state during the second time interval based on the control signal.

9. The apparatus of claim 1, wherein the impedance matching circuit is configured to be coupled between the transducer element and a node that is coupled to the transmitter and the receiver.

10. The apparatus of claim 7, wherein the bypass circuit comprises a switching circuit that is coupled in parallel across the first portion of the impedance matching circuit.

11. The apparatus of claim 1, wherein:

the first portion of the impedance matching circuit is associated with a first voltage drop; and the second portion of the impedance matching circuit is associated with a second voltage drop that is less than the first voltage drop.

12. The apparatus of claim 9, wherein the transducer module comprises a second impedance matching circuit that is coupled between the node and an amplifier of the receiver.

13. The apparatus of claim 1, wherein:

the transducer module comprises a transducer array module configured to be connected to at least one connector of the ultrasound system; and the transducer array module comprises the transducer element, the impedance matching circuit, at least a portion of the transmitter, and at least a portion of the receiver.

14. The apparatus of claim 1, wherein the transducer module comprises:

a transducer array module comprising the transducer element;

an interface circuit comprising the impedance matching circuit; and at least one connector configured to couple the transducer array module to the interface circuit.

15. A method for enhancing sensitivity of an ultrasound system, the method comprising:

propagating a version of an ultrasound transmit signal provided by a transmitter of the ultrasound system through first and second portions of an impedance matching circuit of a transducer module of the ultrasound system to a transducer element of the transducer module, the impedance matching circuit comprising at least one series component;

transmitting the ultrasound transmit signal using the transducer element;

receiving an ultrasound receive signal using the transducer element; and propagating a version of the ultrasound receive signal from the transducer element to a receiver of the ultrasound system in a manner that bypasses the first portion of the at least one series component of the impedance matching circuit and that passes through the second portion of the at least one series component.

16. The method of claim 15, wherein:

the propagating of the version of the ultrasound transmit signal comprises providing a first impedance between two nodes associated with the at least one series component; and the propagating of the version of the ultrasound receive signal comprises providing a second impedance between the two nodes associated with the at least one series component, the second impedance being less than the first impedance.

17. The method of claim 15, wherein:

the at least one series component of the impedance matching circuit comprises an inductor;

the propagating of the version of the ultrasound transmit signal comprises propagating the version of the ultrasound transmit signal through the first and second portions of the inductor; and the propagating the version of the ultrasound receive signal comprises:

propagating the version of the ultrasound receive signal through the second portion of the inductor; and causing the ultrasound receive signal to bypass the first portion of the inductor.

18. The method of claim 15, wherein:

the at least one series component of the impedance matching circuit comprises a first series component and a second series component; and the propagating of the version of the ultrasound receive signal comprises propagating the version of the ultrasound receive signal from the transducer element to the receiver in a manner that bypasses the first series component and passes through the second series component.

19. The method of claim 15, wherein:

the propagating of the version of the ultrasound transmit signal further comprises passing the version of the ultrasound transmit signal through a node that is coupled between the impedance matching circuit and the transmitter; and the propagating of the version of the ultrasound receive signal further comprises passing the version of the ultrasound receive signal through the node that is coupled between the impedance matching circuit and the receiver.

20. The method of claim 19, wherein the propagating of the version of the ultrasound receive signal further comprises propagating the version of the ultrasound receive signal through a second impedance matching circuit that is between the node and a low-noise amplifier of the receiver.

* * * * *